(12) United States Patent
Mukhanov et al.

(10) Patent No.: US 10,460,796 B1
(45) Date of Patent: Oct. 29, 2019

(54) SYSTEM AND METHOD FOR CRYOGENIC HYBRID TECHNOLOGY COMPUTING AND MEMORY

(71) Applicant: Hypres, Inc., Elmsford, NY (US)

(72) Inventors: Oleg A. Mukhanov, Putnam Valley, NY (US); Alexander F. Kirichenko, Pleasantville, NY (US); Igor V. Vernik, Yorktown Heights, NY (US); Ivan P. Nevirkovets, Evanston, IL (US); Alan M. Kadin, Princeton Junction, NJ (US)

(73) Assignee: SeeQC, Inc., Elmsford, NY (US)

( * ) Notice: Subject to any disclaimer, the term of this patent is extended or adjusted under 35 U.S.C. 154(b) by 0 days.

(21) Appl. No.: 15/888,601

(22) Filed: Feb. 5, 2018

Related U.S. Application Data

(63) Continuation of application No. 15/374,618, filed on Dec. 9, 2016, now Pat. No. 9,887,000, which is a
(Continued)

(51) Int. Cl.
*G11C 11/44* (2006.01)
*G11C 11/16* (2006.01)

(52) U.S. Cl.
CPC ............ *G11C 11/44* (2013.01); *G11C 11/161* (2013.01); *G11C 11/1653* (2013.01); *G11C 11/1673* (2013.01)

(58) Field of Classification Search
CPC ... G11C 11/44; G11C 11/161; G11C 11/1653; G11C 11/1673
(Continued)

(56) References Cited

U.S. PATENT DOCUMENTS

| 4,028,714 A | 6/1977 | Henkels |
| 4,360,898 A | 11/1982 | Faris |

(Continued)

FOREIGN PATENT DOCUMENTS

| WO | WO2002069498 | 2/2002 |
| WO | WO2013025994 | 8/2012 |

(Continued)

OTHER PUBLICATIONS

R Service, "Whatll It Take to Go Exascale", Science Magazine, vol. 335, p. 394, Jan. 27, 2012.
(Continued)

*Primary Examiner* — Huan Hoang
(74) *Attorney, Agent, or Firm* — Tully Rinckey PLLC; Steven M. Hoffberg

(57) ABSTRACT

A system and method for high-speed, low-power cryogenic computing are presented, comprising ultrafast energy-efficient RSFQ superconducting computing circuits, and hybrid magnetic/superconducting memory arrays and interface circuits, operating together in the same cryogenic environment. An arithmetic logic unit and register file with an ultrafast asynchronous wave-pipelined datapath is also provided. The superconducting circuits may comprise inductive elements fabricated using both a high-inductance layer and a low-inductance layer. The memory cells may comprise superconducting tunnel junctions that incorporate magnetic layers. Alternatively, the memory cells may comprise superconducting spin transfer magnetic devices (such as orthogonal spin transfer and spin-Hall effect devices). Together, these technologies may enable the production of an advanced superconducting computer that operates at clock speeds up to 100 GHz.

20 Claims, 29 Drawing Sheets

Related U.S. Application Data continuation of application No. 14/643,078, filed on Mar. 10, 2015, now Pat. No. 9,520,180.

(60) Provisional application No. 61/951,169, filed on Mar. 11, 2014.

(58) Field of Classification Search
USPC ......................................................... 365/162
See application file for complete search history.

(56) References Cited

U.S. PATENT DOCUMENTS

| | | | |
|---|---|---|---|
| 4,430,662 A | 2/1984 | Jillie, Jr. et al. | |
| 4,499,199 A | 2/1985 | McDaniel | |
| 4,509,146 A | 4/1985 | Wang et al. | |
| 4,589,161 A | 5/1986 | Kochte et al. | |
| 4,633,439 A | 12/1986 | Harada et al. | |
| 5,055,158 A | 10/1991 | Gallagher et al. | |
| 5,126,598 A | 6/1992 | Kotani | |
| 5,365,476 A | 11/1994 | Mukhanov | |
| 5,388,068 A | 2/1995 | Ghoshal et al. | |
| 5,406,201 A | 4/1995 | Kiryu et al. | |
| 5,962,865 A | 10/1999 | Kerber et al. | |
| 6,420,895 B1 | 7/2002 | Herr et al. | |
| 6,459,097 B1 | 10/2002 | Zagoskin | |
| 6,495,854 B1 | 12/2002 | Newns et al. | |
| 6,563,310 B2 | 5/2003 | Zagoskin | |
| 6,563,311 B2 | 5/2003 | Zagoskin | |
| 6,580,510 B2 | 6/2003 | Nawracala | |
| 6,627,915 B1 | 9/2003 | Ustinov et al. | |
| 6,649,929 B2 | 11/2003 | Newns et al. | |
| 6,653,952 B2 | 11/2003 | Hayami et al. | |
| 6,803,599 B2 | 10/2004 | Amin et al. | |
| 6,812,464 B1 | 11/2004 | Sobolewski et al. | |
| 6,838,694 B2 | 1/2005 | Esteve et al. | |
| 6,865,639 B2 | 3/2005 | Herr | |
| 6,917,537 B2 | 7/2005 | Bunyk | |
| 6,936,841 B2 | 8/2005 | Amin et al. | |
| 6,960,929 B2 | 11/2005 | Bedard | |
| 6,979,835 B1 | 12/2005 | Yu et al. | |
| 7,049,593 B2 | 5/2006 | Sobolewski et al. | |
| 7,060,508 B2 | 6/2006 | Kerber | |
| 7,105,853 B2 | 9/2006 | Kerber | |
| 7,135,701 B2 | 11/2006 | Amin et al. | |
| 7,170,778 B2 | 1/2007 | Kent et al. | |
| 7,253,654 B2 | 8/2007 | Amin | |
| 7,280,623 B2 | 10/2007 | Gupta et al. | |
| 7,307,275 B2 | 12/2007 | Lidar et al. | |
| 7,335,909 B2 | 2/2008 | Amin et al. | |
| 7,362,125 B2 | 4/2008 | Gupta et al. | |
| 7,376,691 B2 | 5/2008 | Jung et al. | |
| 7,418,283 B2 | 8/2008 | Amin | |
| 7,440,490 B2 | 10/2008 | Kidiyarova-Shevchenko et al. | |
| 7,443,719 B2 | 10/2008 | Kirichenko et al. | |
| 7,459,927 B2 | 12/2008 | Bedard | |
| 7,533,068 B2 | 5/2009 | Maassen van den Brink et al. | |
| 7,605,600 B2 | 10/2009 | Harris | |
| 7,615,385 B2 | 11/2009 | Tolpygo | |
| 7,701,286 B2 | 4/2010 | Gupta et al. | |
| 7,724,020 B2 | 5/2010 | Herr | |
| 7,839,675 B2 | 11/2010 | Koo et al. | |
| 7,847,615 B2 | 12/2010 | Yorozu et al. | |
| 7,876,869 B1 | 1/2011 | Gupta | |
| 7,889,992 B1 | 2/2011 | DiVincenzo et al. | |
| 7,903,456 B2 | 3/2011 | Kirichenko et al. | |
| 7,977,064 B2 | 7/2011 | Zhang et al. | |
| 7,991,013 B2 | 8/2011 | Gupta et al. | |
| 8,045,660 B1 | 10/2011 | Gupta | |
| 8,055,235 B1 | 11/2011 | Gupta et al. | |
| 8,116,122 B2 | 2/2012 | Li et al. | |
| 8,130,880 B1 | 3/2012 | Gupta | |
| 8,159,825 B1 | 4/2012 | Dotsenko | |
| 8,234,103 B2 | 7/2012 | Biamonte et al. | |
| 8,247,799 B2 | 8/2012 | Bunyk et al. | |
| 8,249,540 B1 | 8/2012 | Gupta et al. | |
| 8,260,143 B2 | 9/2012 | Gupta et al. | |
| 8,260,144 B2 | 9/2012 | Gupta et al. | |
| 8,260,145 B2 | 9/2012 | Gupta et al. | |
| 8,270,209 B2 | 9/2012 | Herr et al. | |
| 8,283,943 B2 | 10/2012 | van den Brink et al. | |
| 8,284,585 B2 | 10/2012 | Maekawa et al. | |
| 8,301,104 B1 | 10/2012 | Gupta et al. | |
| 8,301,214 B1 | 10/2012 | Tolpygo et al. | |
| 8,383,426 B1 | 2/2013 | Tolpygo | |
| 8,401,509 B1 | 3/2013 | Gupta et al. | |
| 8,437,168 B2 | 5/2013 | Maekawa et al. | |
| 8,437,818 B1 | 5/2013 | Tolpygo et al. | |
| 8,462,889 B2 | 6/2013 | Gupta | |
| 8,473,818 B2 | 6/2013 | Mangione-Smith et al. | |
| 8,489,163 B2 | 7/2013 | Herr et al. | |
| 8,498,491 B1 | 7/2013 | Steffens | |
| 8,514,986 B2 | 8/2013 | Gupta | |
| 8,521,117 B1 | 8/2013 | Gupta et al. | |
| 8,547,732 B2 | 10/2013 | Bulzacchelli et al. | |
| 8,565,844 B2 | 10/2013 | Smith | |
| 8,571,614 B1 | 10/2013 | Mukhanov et al. | |
| 8,610,453 B2 | 12/2013 | Herr | |
| 8,611,117 B2 | 12/2013 | Kim et al. | |
| 9,520,180 B1 | 12/2016 | Mukhanov et al. | |
| 9,595,970 B1 * | 3/2017 | Reohr | H03K 19/195 |
| 9,887,000 B1 | 2/2018 | Mukhanov et al. | |
| 2004/0201400 A1 | 10/2004 | Herr | |
| 2010/0246250 A1 * | 9/2010 | Chen | G11C 7/08 365/171 |
| 2011/0089405 A1 | 4/2011 | Ladizinsky et al. | |
| 2012/0077689 A1 | 3/2012 | Sarwal et al. | |
| 2012/0184445 A1 | 7/2012 | Mukhanov et al. | |
| 2012/0294078 A1 | 11/2012 | Kent et al. | |
| 2012/0302446 A1 | 11/2012 | Ryazanov et al. | |
| 2012/0314490 A1 | 12/2012 | Okhi et al. | |
| 2013/0143744 A1 | 6/2013 | Marsili et al. | |
| 2014/0001524 A1 | 1/2014 | Manipatruni et al. | |
| 2014/0015074 A1 | 1/2014 | Bedau et al. | |
| 2014/0035617 A1 | 2/2014 | Raychowdhury et al. | |

FOREIGN PATENT DOCUMENTS

| | | |
|---|---|---|
| WO | WO2013180946 | 5/2013 |
| WO | WO2014025838 | 8/2013 |

OTHER PUBLICATIONS

D.S. Holmes, et al., "Energy-Efficient Superconducting Computing—Power Budgets and Requirements", IEEE Transactions on Applied Superconductivity, vol. 23, No. 3, 1701610 (Jun. 2013).

W. Anacker, "Josephson Computer Technology: An IBM Research Project", IBM Journal of Research and Development, vol. 24, No. 2, p. 107 (Mar. 1980).

K.K. Likharev and V.K. Semenov, "RSFQ Logic/Memory Family: A New Josephson Junction Technology for Sub-Terahertz-Clock Frequency Digital Systems", IEEE Transactions on Applied Superconductivity, vol. 1, No. 1, p. 3 (Mar. 1991).

O. Mukhanov, et al., "Superconductor Digital-RF Receiver Systems", IEICE Transactions on Electronics, vol. E91-C, p. 306 (2008).

A. Fujimaki et al., Bit-serial single flux quantum microprocessor CORE, IEICE Transactions on Electronics, vol. E91-C, p. 342 (2008).

A. Dorojevets, et al., Data-flow microarchitecture for wide datapath RSFQ processors, IEEE Transactions on Applied Superconductivity, vol. 21, No. 3, p. 787 (Jun. 2011).

M. Dorojevets, et al., "8-Bit Asynchronous Sparse-Tree Superconductor RSFQ Arithmetic-Logic Unit With a Rich Set of Operations", IEEE Trans Appl. Supercond., vol. 23, No. 3, 1700104 (Jun. 2013).

O. Mukhanov, "Energy-efficient single flux quantum technology", IEEE Trans. Appl. Supercond., vol. 21, p. 760 (2011).

Q. Herr, et al., "Ultra-low-power superconductor logic", Journal of Applied Physics, vol. 109, 103903 (2011).

M. Tanaka, et al., "Low-energy-consumption RSFQ circuits driven by low voltages", IEEE Trans. Appl. Supercond., vol. 23, 1701104 (Jun. 2013).

(56) References Cited

OTHER PUBLICATIONS

D. Kirichenko, et al., "Zero static power dissipation biasing of RSFQ circuits", IEEE Trans. Appl. Supercond., vol. 21, p. 776 (Jun. 2011).
M. Volkmann, et al., "Implementation of energy efficient single flux quantum digital circuits with sub-aJ/bit operation", Supercond. Science Technology, vol. 26, 015002 (2013).
M. Volkmann, et al., "Experimental investigation of energy-efficient digital circuits based on eSFQ logic", IEEE Trans. Appl. Supercond., vol. 23, 1301505 (Jun. 2013).
M. Volkmann, et al., "Operation of practical eSFQ circuits," Proc. IEEE 14th Int. Supercond. Eloectronics Conf. (2013).
I. Vernik, et al., "Magnetic Josephson junctions with superconducting interlayer for cryogenic memory", IEEE Trans. Appl. Supercond., vol. 23, 1701208 (2013).
T. Larkin, et al., "Ferromagnetic Josephson switching device with high characteristic voltage", Appl. Physics Letters, vol. 100, 222601 (May 2012).
S. Bakurskiy, et al., "Theoretical model of superconducting SIsFS devices", Appl. Physics Letters, vol. 102, 192603 (May 2003).
V. Ryazanov, et al., "Magnetic Josephson junction technology for digital and memory applications", Physics Procedia, vol. 36, p. 35 (2012).
Prokopenko, et al., "DC and RF measurements of superconducting-ferromagnetic multiterminal devices", Proc. IEEE 14th Int. Superconductive Electronics Conf. (2013).
A. Kadin, et al., "Current leads and optimized thermal packaging for superconducting systems on multistage cryocoolers", IEEE Trans. Appl. Supercond., vol. 17, p. 975 (2007).
R. Webber, et al., "Ultra-low-heat-leak YBCO superconducting leads for cryoelectronic applications", IEEE Trans. Appl. Supercond., vol. 19, p. 999 (2009).
A. Pan, et al., "Development of energy-efficient cryogenic leads with high-temperature superconducting films on ceramic substrates", Physics Procedia, vol. 36 (2012).
O. Mukhanov, et al., "Development of energy-efficient cryogenic-optical data link", Proc. IEEE 14th Int. Superconductive Electronic Conference (2013).
Chen et al., "Kinetic Inductance Memory Cell", IEEE Trans. Appl. Supercond., vol. 2, p. 95 (1992).
Johnson et al., "Anomalous current dependence of kinetic inductance of ultrathin NbN meander lines", IEEE Trans. Appl. Supercond., vol. 7, p. 3492 (1997).
L. Ye et al., "Spin-transfer switching of orthogonal spin-valve devices at cryogenic temperatures", J. Applied Physics, vol. 115, 17C725 (2014).
A. McCaughan and K. Berggren, "A Superconducting Nanowire Three-Terminal Electrothermal Device", Nano Letters, vol. 14, No. 10, pp. 5748-5753 (Sep. 2014).
O. Quaranta, et al., "Superconductive three-terminal amplifier/discriminator", IEEE Trans. Appl. Supercond., vol. 19, p. 367 (2009).
D. Gupta, et al., "High-speed inter-chip data transmission technology for superconducting multi-chip modules", IEEE Trans. Appl. Supercond., vol. 11, p. 731 (2001).
S. Narayana, et al., "Design and Testing of high-speed interconnects for superconducting multi-chip modules", Supercond. Sci. Technol., vol. 25, 105012 (2012).
Bakurskiy et al., "Theoretical model of superconducting spintronic SIsFS devices", Appl. Phys. Lett., vol. 102, 192603 (2013).
Vernik et al., "Magnetic Josephson junctions with superconducting interlayer for cryogenic memory", IEEE Trans. Appl. Supercond., vol. 23, 1701208 (2013).
L. Uspenskaya, et al., "Magnetic patterns and flux pinning in PdFe—Nb hybrid structures", JETP Lett., vol. 97, p. 155 (2013).
Nevirkovets, "Hybrid superconductor-ferromagnet transistor-like device", Supercond. Sci. Technol., vol. 24, 024009 (2011).
D. Gupta et al., "Modular Multi-function Digital-RF Receiver Systems," IEEE Trans. Appl. Supercond., vol. 21, p. 883 (2011).
Y. Polyakov, "3D active demagnetization of cold magnetic shields", IEEE Trans. Appl. Supercond., vol. 21, p. 724 (2011).
Herr Bunyk, "Implementation and application of first-in, first-out buffers", IEEE Trans. Appl. Supercond., vol. 13, p. 563, 2002.
M. Dorojevets, et al., "16-Bit Wave-Pipelined Sparse-Tree RSFQ Adder", IEEE Trans. Appl. Supercond. vol. 23, Art. 1700605, Inspec 13233919 (Dec. 12, 2012), DOI:10.1109/TASC.2012.2233846.
en.wikipedia.org/wiki/Spin.sub—valve (Apr. 17, 2014).
en.wikipedia.org/wiki/Kinetic.sub.—inductance (Jan. 15, 2015.

* cited by examiner

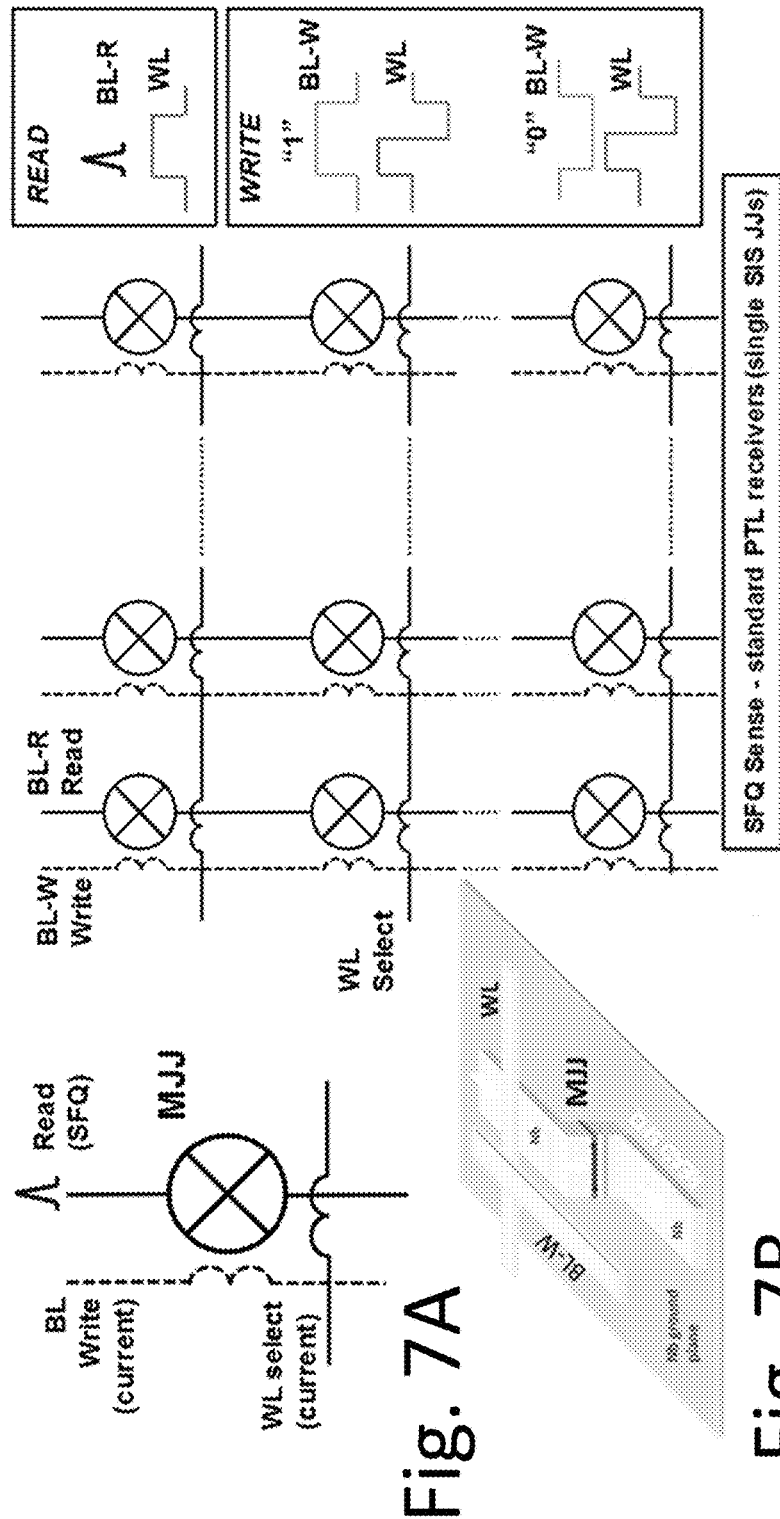

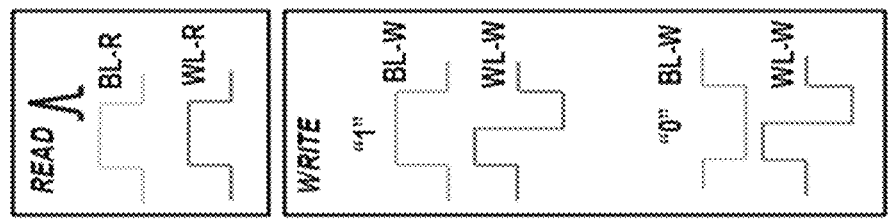
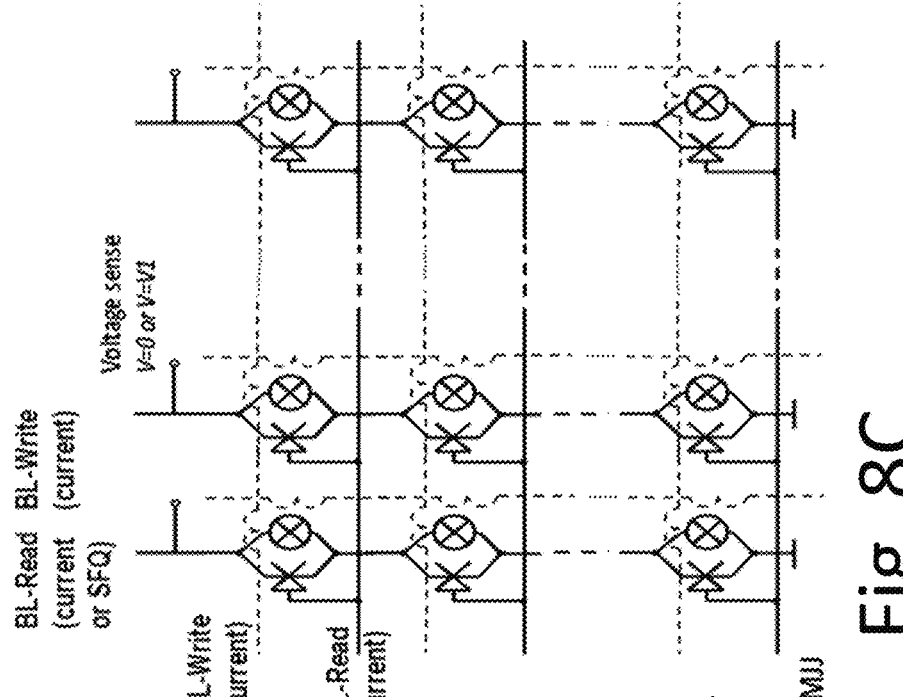
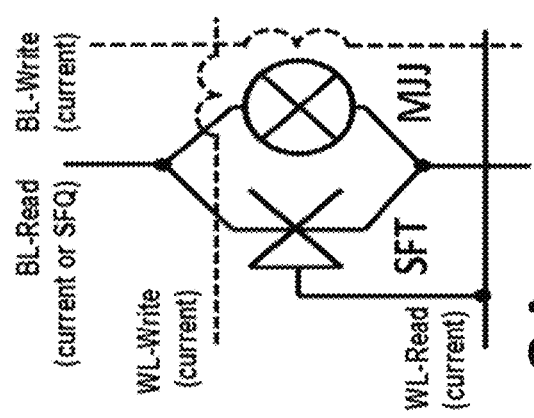
Fig. 8A
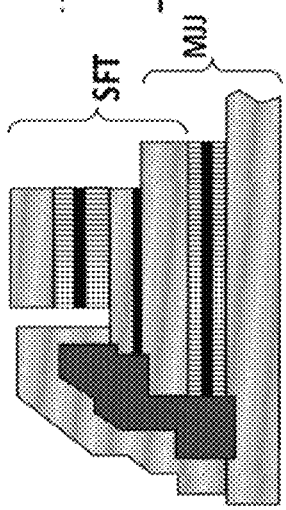
Fig. 8B
Fig. 8C

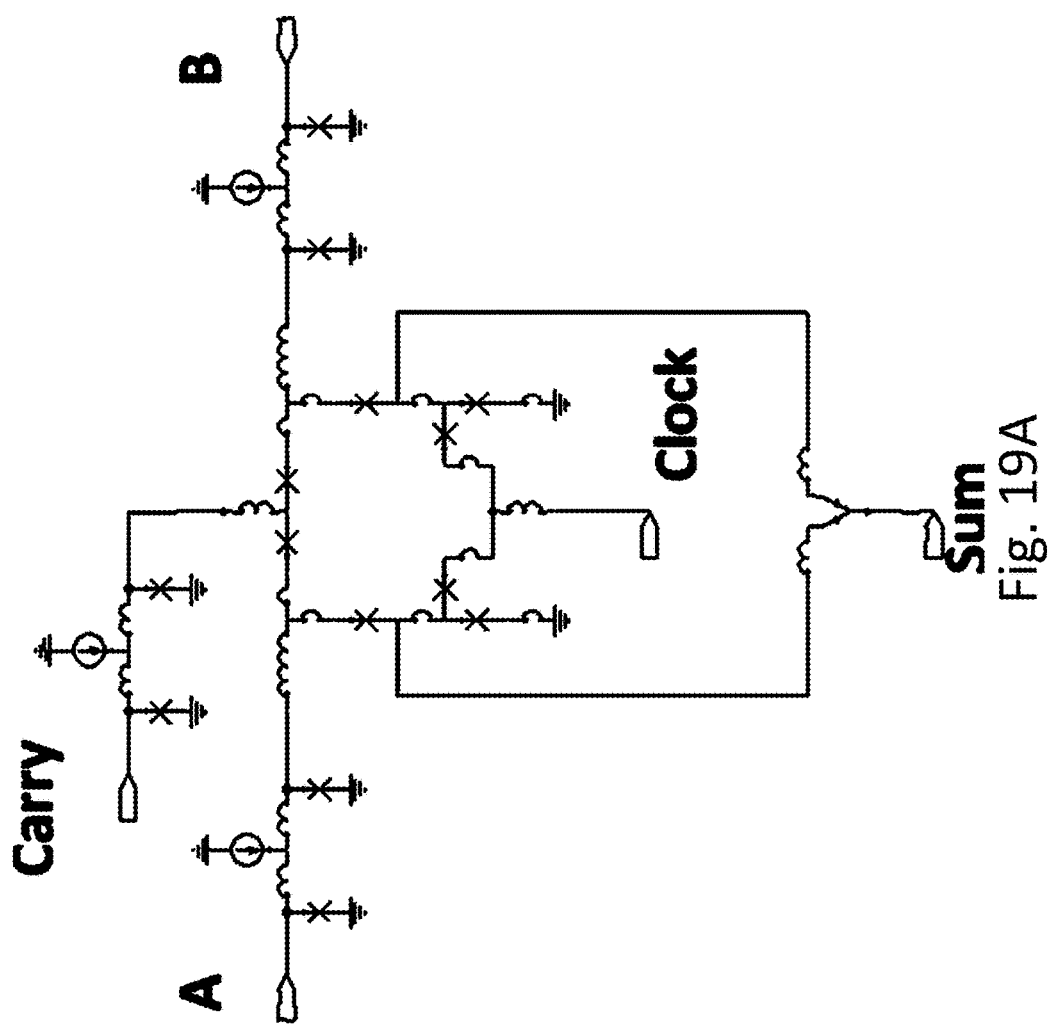

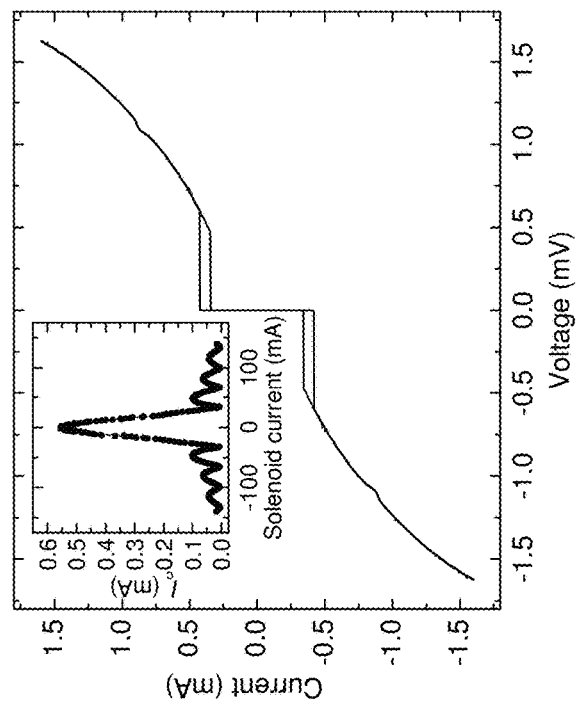
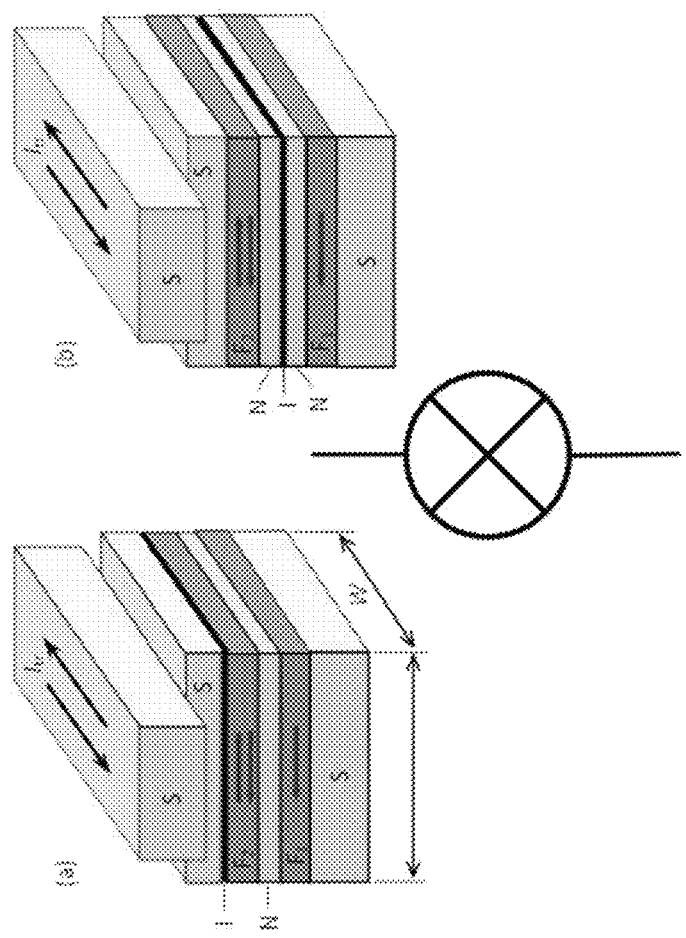
Fig. 24A  Fig. 24B  Fig. 24C

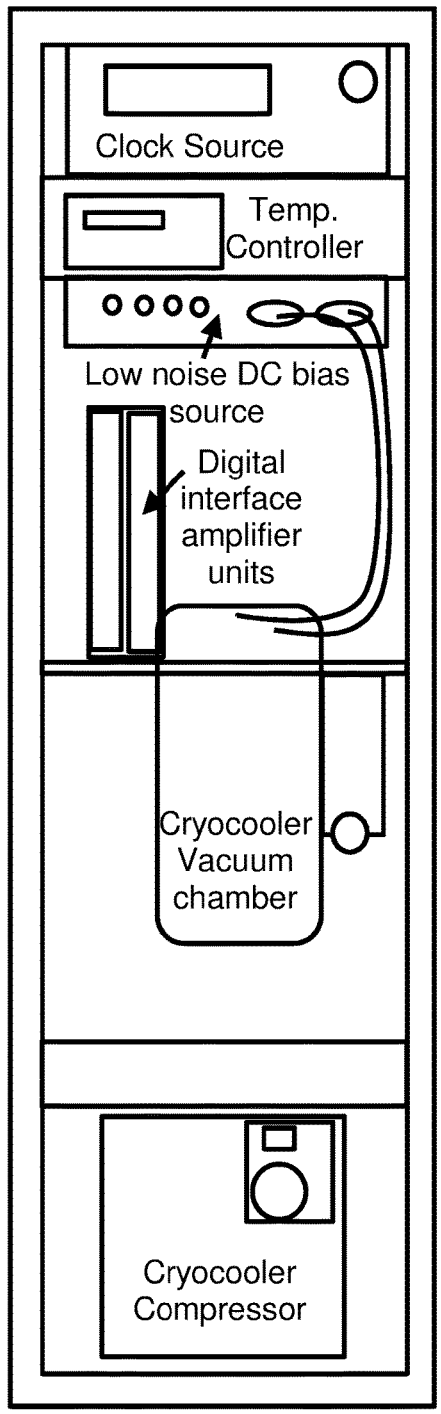
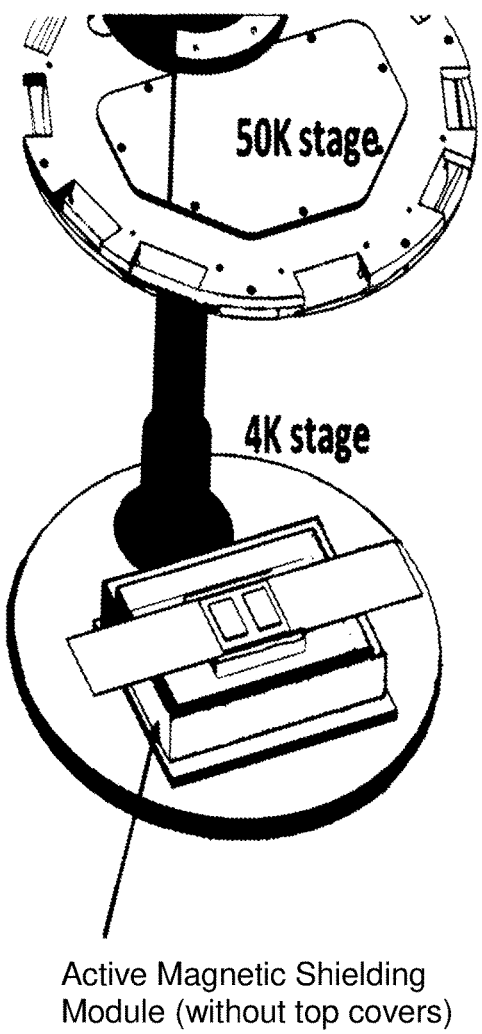
Fig. 28A
Fig. 28B

SYSTEM AND METHOD FOR CRYOGENIC HYBRID TECHNOLOGY COMPUTING AND MEMORY

CROSS REFERENCE TO RELATED APPLICATION

The present application is a Continuation of U.S. patent application Ser. No. 15/374,618, filed Dec. 9, 2016, now U.S. Pat. No. 9,887,000, issued Feb. 6, 2018, which is a Continuation of U.S. patent application Ser. No. 14/643,078, filed Mar. 10, 2015, now U.S. Pat. No. 9,520,180, issued Dec. 13, 2016, which claims benefit of priority from U.S. Provisional Patent Application 61/951,169, filed Mar. 11, 2014, the entirety of which are each expressly incorporated herein by reference.

BACKGROUND OF THE INVENTION

The explosive growth of the Internet has transformed data centers into large industrial-scale computer facilities with extraordinarily high energy demands. From Google and Facebook to banking, cloud computing and supercomputing, an average data center already uses as much electricity as a medium-size town. In Silicon Valley, data centers are also listed as the top air polluters from backup diesel exhausts. Already by 2012, the energy costs for a data center were estimated to exceed the cost of the original capital investment over its useful life. The carbon footprint of data centers is expected to exceed that of the airline industry by 2020. For 2011, the Facebook carbon footprint was ~285,000 metric tons of $CO_2$ equivalent. For 2010, that of Google was five times higher—1,500,000 tons. Energy considerations are forcing the construction of new data centers in areas where the climate helps cooling and electricity is cheaper. A recent Facebook 120 MW data center was built just south of the Arctic Circle in Sweden, close to a hydropower station producing twice as much electricity as the Hoover Dam in Nevada. Besides just high energy costs and adverse environmental impact, there is a compelling technical reason to improve the energy efficiency of computing technologies. The development of the next generations of high-end computers (e.g., exascale supercomputers and beyond, where exa=$10^{18}$) will not be possible unless a significant improvement in energy efficiency is achieved over the technology available today. See, for example, R. Service, "What'll It Take to Go Exascale", Science Magazine, vol. 335, p. 394, Jan. 27, 2012, expressly incorporated herein by reference. For a computer rated at 1 ExaFLOPS ($10^9$ Giga FLoating-point OPerations per Second), this requires >50 Giga-FLOPS/W. As of November 2012, the fastest supercomputer Titan (Cray XK7) had ~2 GigaFLOPS/W (~20 PetaFLOPS at ~10 MW). The power dissipation target for a future exascale supercomputer is very stringent—no more than 20 MW, which is just two times larger than that of Titan with ~1/50 ExaFLOPS.

The heart of the problem is in the relatively low energy efficiency of current computer circuit technologies that consume too much power for computing, storing and moving data between processors and memories. Despite the fact that Moore's law continues to enable even more transistors per chip, Dennard scaling (the simultaneous reduction of CMOS threshold and bias voltages commensurate with device size reduction) ended a few years ago. Now every new CMOS process generation has higher power density, and peak power requirements are increasing at a rate far exceeding the ability to remove heat. This is the reason that energy efficiency rather than switching speed or circuit area has now become the dominant metric in computing performance, from hand-held portable devices to high-end, large-scale supercomputers.

Conventional approaches are unlikely to yield sufficient reduction in power density. In contrast, superconducting single-flux quantum (SFQ) circuits, by virtue of their inherent low power dissipation, high speed, and lossless interconnect, present an excellent opportunity to dramatically increase the energy efficiency of high-end computing applications. See, for example, D. S. Holmes, et al., "Energy-Efficient Superconducting Computing—Power Budgets and Requirements", IEEE Transactions on Applied Superconductivity, vol. 23, no. 3, 1701610 (June 2013), expressly incorporated herein by reference. This should dramatically enhance the energy-efficiency of data centers and enable new generations of supercomputers.

Ever since the late 1960s, superconducting Josephson junction integrated circuits have been considered as possible candidates for high-speed, low-power computing. See, for example, W. Anacker, "Josephson Computer Technology: An IBM Research Project", IBM Journal of Research and Development, vol. 24, no. 2, p. 107 (March 1980), expressly incorporated herein by reference. See also U.S. Pat. Nos. 5,365,476; 4,509,146; 4,360,898; 4,633,439; 5,126,598; 5,388,068; all expressly incorporated herein by reference. This technology produced circuits with very low power densities and clock rates of several GHz, fabricated using a robust integrated circuit process based on niobium Josephson junctions, typically operating at a temperature near 4 K. For more on the niobium IC process, see e.g., U.S. Pat. Nos. 4,430,662; 7,615,385; 8,383,426; 4,499,199; 4,589,161; 7,060,508; 7,105,853; 8,301,214; 8,437,818; 2011/0089405; 5,055,158; all expressly incorporated herein by reference. However, these earlier circuits were superseded by another much faster logic family also based on Josephson junctions, superconducting rapid single-flux quantum (RSFQ) logic, invented in the mid-1980s, which promised digital circuits with clock rates up to 100 GHz. See K. K. Likharev and V. K. Semenov, "RSFQ Logic/Memory Family: A New Josephson Junction Technology for Sub-Terahertz-Clock Frequency Digital Systems", IEEE Transactions on Applied Superconductivity, vol. 1, no. 1, p. 3 (March 1991), expressly incorporated herein by reference. This enabled the development of ultrafast digital signal processing circuits by the mid-2000s, and today, cryogenic RSFQ Digital-RF receivers operating with 30 GHz clock frequency are available for wide-bandwidth satellite communications and signal intelligence applications. See, for example, O. Mukhanov, et al., "Superconductor Digital-RF Receiver Systems", IEICE Transactions on Electronics, vol. E91-C, p. 306 (2008), expressly incorporated herein by reference. See also U.S. Pat. Nos. 8,462,889; 8,260,143; 8,260,144; 8,260,145; 8,521,117; 8,055,235; 8,521,117; 8,301,104; 8,514,986; 7,876,869; 8,045,660; 8,130,880; 8,514,986; 7,280,623; 8,249,540; 8,401,509; 7,701,286; 7,362,125; 7,991,013; 8,498,491; all expressly incorporated herein by reference. Furthermore, various prototypes of high-speed processors, data and signal processing modules have also been demonstrated. See, for example, A. Fujimaki et al., "Bit-serial single flux quantum microprocessor CORE, IEICE Transactions on Electronics, vol. E91-C, p. 342 (2008); M. Dorojevets, et al., Data-flow microarchitecture for wide datapath RSFQ processors", IEEE Transactions on Applied Superconductivity, vol. 21, no. 3, p. 787 (June 2011); M. Dorojevets, et al., "8-Bit Asynchronous Sparse-Tree Superconductor RSFQ Arithmetic-Logic Unit With a Rich Set of Operations", IEEE Trans. Appl. Supercond., vol. 23, no. 3, 1700104 (June 2013); all expressly incorporated herein by reference. See also U.S. Pat. Nos. 7,376,691; 7,440,490; 6,917,537; 6,865,639; 7,443,719; 7,903,456; 6,960,929; 7,459,927; also WO2002/069498; all expressly incorporated herein by reference.

RSFQ logic is based on exploiting single quanta of magnetic flux to encode clock and data, corresponding to a fast voltage pulse is generated with quantized area $$\int V(t)dt = \Phi_0 = h/2e = 2.06 \times 10^{-15} \text{ Wb} = 2.06 \text{ mV-ps},$$

known as a single flux quantum or SFQ. For a typical Josephson junction, such a pulse is created with pulse height ~1 mV and pulsewidth ~2 ps. The energy consumed during this switching event is of the order of $I_C \times \Phi_0 \sim 10^{-19}$ J assuming $I_C \sim 0.1$ mA (chosen to exceed thermal noise at 4 K). Therefore, the gate switching energy is directly related to thermal energy rather than device dimensions as in CMOS. The picosecond quantized SFQ voltage pulses were proven to propagate ballistically on-chip and between chips via superconducting microstrip lines (with low loss and dispersion) without the need for amplification, and with speeds close to the speed of light. This is the key advantage of superconducting technology over CMOS, in which the data movement energy is proportional to the length of interconnect and currently represents the dominant share of the consumed energy.

Until recently, the inherently low switching power of conventional RSFQ logic was overwhelmed by the static power dissipation in the network of bias resistors used to distribute the required amounts of DC bias current for RSFQ gates. This overhead power was dissipated all the time regardless of circuit operation status. Recent efforts have resulted in significant reduction and even complete elimination of the static power dissipation in SFQ circuits. See, e.g., O. Mukhanov, "Energy-efficient single flux quantum technology", IEEE Trans. Appl. Supercond., vol. 21, p. 760 (2011); Q. Herr, et al., "Ultra-low-power superconductor logic", Journal of Applied Physics, vol. 109, 103903 (2011); M. Tanaka, et al., "Low-energy-consumption RSFQ circuits driven by low voltages", IEEE Trans. Appl. Supercond., vol. 23, 1701104 (June 2013), all expressly incorporated herein by reference. See also U.S. Pat. Nos. 8,571,614; 7,724,020; 7,977,064; 8,610,453; 8,489,163; all expressly incorporated herein by reference. In particular, the new energy-efficient RSFQ logic families (eSFQ and ERSFQ) have zero static power dissipation while retaining all the advantages of conventional RSFQ logic. In these circuits, resistors are replaced with superconducting Josephson junctions performing the role of current limiters. To date, a number of successful eSFQ and ERSFQ integrated circuits have been demonstrated. See, for example, the following articles, all expressly incorporated herein by reference: D. Kirichenko, et al., "Zero static power dissipation biasing of RSFQ circuits", IEEE Trans. Appl. Supercond., vol. 21, p. 776 (June 2011); M. Volkmann, et al., "Implementation of energy efficient single flux quantum digital circuits with sub-aJ/bit operation", Supercond. Science & Technology, vol. 26, 015002 (2013); M. Volkmann, et al., "Experimental investigation of energy-efficient digital circuits based on eSFQ logic", IEEE Trans. Appl. Supercond., vol. 23, 1301505 (June 2013); M. Volkmann, et al., "Operation of practical eSFQ circuits," Proc. IEEE 14th Int. Supercond. Electronics Conf. (2013).

For many years the prospects of superconducting technology for high-end computing have been stymied by the relatively low capacity of superconducting memories. Very recently, new memory approaches based on magnetic Josephson junctions (MJJs) and on cryogenic magnetic elements have been proposed and are now being extensively studied. See US Patents 2012/0184445; 2012/0302446; 8,270,209; 8,547,732; 2012/0314490; see also WO2013/025994; WO2013/180946; all expressly incorporated herein by reference. In MJJs, critical current can switch between two distinct states corresponding to logical '0' and '1' depending on the magnetization of the ferromagnetic layer (s). Memory circuits using MJJs can be made that are electrically and physically compatible with SFQ circuits. This allows a co-fabrication of memory and digital circuits on the same chip, leading to significant processor-memory architecture advantages relevant to high-end computing. See, e.g., the following papers, expressly incorporated herein by reference: I. Vernik, et al., "Magnetic Josephson junctions with superconducting interlayer for cryogenic memory", IEEE Trans. Appl. Supercond., vol. 23, 1701208 (2013); T. Larkin, et al., "Ferromagnetic Josephson switching device with high characteristic voltage", Appl. Physics Letters, vol. 100, 222601 (May 2012); S. Bakurskiy, et al., "Theoretical model of superconducting SIsFS devices", Appl. Physics Letters, vol. 102, 192603 (May 2013); V. Ryazanov, et al., "Magnetic Josephson junction technology for digital and memory applications", Physics Procedia, vol. 36, p. 35 (2012); G. Prokopenko, et al., "DC and RF measurements of superconducting-ferromagnetic multiterminal devices", Proc. IEEE 14th Int. Superconductive Electronics Conf. (2013).

Cooling infrastructure for modern data centers accounts on average for 25-50% of total power. For superconductor systems, the energy efficiency of the entire cryosystem is paramount. The efficiency of available 4 K cryocoolers can reach <400 W/W for higher-capacity units (600-900 W) relevant for high-end computing systems, such as a Linde LR280 cryocooler with 360 W/W efficiency. A future cryogenic supercomputer will have a much smaller footprint than present systems, as the main computing part will occupy a single cryocooler (or perhaps two for redundancy). Besides the cryocooler, the cryosystem energy efficiency depends on minimizing energy losses and heat leaks in the input/output data links and power delivery network. Practical experience with smaller superconductor electronics systems helped the development of a hybrid-temperature hybrid-technology system integration approach to maximize the cryosystem energy efficiency. The first generation of high-temperature superconductor (HTS) cables for DC bias current delivery were successfully demonstrated to reduce heat leaks in RSFQ electronic cryosystems. See, for example, the following articles, expressly incorporated herein by reference: A. Kadin, et al., "Current leads and optimized thermal packaging for superconducting systems on multistage cryocoolers", IEEE Trans. Appl. Supercond., vol. 17, p. 975 (2007); R. Webber, et al., "Ultra-low-heat-leak YBCO superconducting leads for cryoelectronic applications", IEEE Trans. Appl. Supercond., vol. 19, p. 999 (2009); A. Pan, et al., "Development of energy-efficient cryogenic leads with high-temperature superconducting films on ceramic substrates", Physics Procedia, vol. 36 (2012).

Serious development effort is required in order to take advantage of all of the recent advances capable of addressing the runaway power of high-end computing, and getting superconducting technologies into data centers and supercomputers. A central problem is the relatively low complexity and device density of present superconductor integrated circuits, especially compared to current CMOS technology. The available Nb fabrication processes are generally limited to ~1 µm linewidth with just a few Nb layers. It is a priority to develop a high-yield, high integration density, planarized fabrication process with linewidth ~90-250 nm, critical current density $J_C$>10 kA/cm$^2$, and >8-10 Nb wiring layers. Advancing the critical current density to 100 kA/cm$^2$, or using a different junction barrier material than the standard aluminum oxide, is necessary to achieve self-shunted Josephson junctions to eliminate the area-consuming shunting resistors. Another new direction for process development is superconducting-ferromagnetic Josephson junctions (Magnetic Josephson Junctions or MJJs) for magnetic memory and programmable logic. This will enable new programmable functionalities unavailable to superconducting electronics in the past. For example, three-dimensional (3D) integration of processing and memory circuits, fabricated in a single process, should lead to a dramatic gain in the microprocessor performance efficiency, enabling new microarchitectures highly relevant for high-end data-centric computing. All these can be achieved while developing a better understanding of superconductor material issues and actively employing already-developed semiconductor techniques and equipment.

The recent innovations in energy-efficient SFQ digital circuits, eliminating static power dissipation of conventional RSFQ logic, are highly promising. Further reduction of dynamic power dissipation can enlarge the advantage of SFQ circuits over the competition. The next logical step is to implement more functionally significant circuits, such as a microprocessor. One of the common traps with any new technology is the attempt to make better versions of existing solutions which were optimized for older existing technology. The RSFQ-type circuits (eSFQ and ERSFQ) are based on sequential logic, which is different from CMOS combinational logic, implying that the implementation of CMOS-inspired processor microarchitectures and algorithms may not be optimal and will lead to an underutilization of technology potential.

The extremely high clock rate (~100 GHz) achievable in RSFQ-type circuits fits better to microarchitectures with a high degree of vectorization. In order to keep the processing pipeline full, one should have a fast memory capable of supplying input data and store the results at the same high data rate. This can be alleviated by clever ways of using the internal gate memory. MJJ-based memory circuits integrated in the immediate proximity of processing modules (e.g., as 3D structures) can be an excellent solution. Recent results in MJJ device development provides a path to development of functional fast and energy-efficient memories, including nonvolatile random access memory (RAM) compatible with energy-efficient (e.g., eSFQ) digital circuits. The impact of integrated MJJ RAM and JJ eSFQ processing blocks is difficult to overestimate. This can also lead to the development of programmable digital logic arrays functionally similar to semiconductor field-programmable gate arrays (FPGAs). In addition, the integrated SFQ circuits and non-superconducting magnetic RAM devices are attractive for higher-capacity memories, e.g., main memories.

An energy-efficient, high-bandwidth data interface to room temperature modules and the optical domain is unavoidable in any high-end computing system. There is a need to develop a technology to convert a low-voltage (~0.3-1.0 mV) electrical digital signal to the optical domain at a high data rate (tens of GHz). This has been a longstanding and extremely difficult problem, which has retarded the integration of ultra-low-power electronics with conventional electronics and fiber-optics. To meet tightly-constrained power budgets, the energy efficiency of data links in exascale systems should be on the order of 2 pJ/bit or less. The degree of amplification at a specific temperature stage can be the guiding principle in the energy-efficiency optimization of data links across different temperature stages available in a cryosystem. HTS multi-bit data cables capable of transmitting low-power signals from 4 K to higher-temperature amplifiers and electro-optical devices (e.g., vertical-cavity surface-emitting lasers, VCSELs) with negligible losses and dispersion will be required. See, for example, O. Mukhanov, et al., "Development of energy-efficient cryogenic-optical data link", Proc. IEEE 14$^{th}$ Int. Superconductive Electronic Conference (2013), expressly incorporated herein by reference.

It is important to distinguish computers based on RSFQ logic from a set of completely different approaches that are also based on cryogenic Josephson junctions, under the heading "quantum computers". RSFQ-based computers are digital computers based on classical bits that assume alternate, and not superposed values. In contrast, quantum computers are based on quantum superposition of bits in two or more quantum states, known as qubits. Both analog and digital processors based on superconducting qubits have been proposed, and in some cases developed. These superconducting quantum computers typically require cooling to extremely low temperatures, less than 0.1 K, much colder than the 4 K typical for classical superconducting niobium RSFQ computers. See, for example, the following US patents, expressly incorporated herein by reference: U.S. Pat. Nos. 7,135,701; 7,418,283; 8,284,585; 8,437,168; 8,247,799; 7,605,600; 8,234,103; 7,335,909; 7,889,992; 6,803,599; 6,936,841; 6,838,694; 7,307,275; 6,495,854; 6,649,929; 6,563,310; 6,563,311; 6,459,097; 7,847,615; 7,533,068; 8,283,943; 6,979,835; 6,627,915; 7,253,654. The design and performance of these superconducting quantum computer systems is completely different from the high-performance superconducting classical computers described herein.

The prior art has not yet effectively solved the problems associated with integrating ultrafast superconducting processors with hybrid superconducting/magnetic memories, cryogenic cooling systems, high-speed input/output devices, and room-temperature processors and networks.

With rising energy costs and technical roadblocks, computing system energy efficiency has become the dominating metric dictating the course of future technology development. Superconducting single-flux quantum processors augmented with superconducting-ferromagnetic memory technology can finally break into prominence by addressing the energy efficiency of high-end computing systems. The key innovations just within the last few years have dramatically increased the potential of superconducting electronics, addressing all known critical problems which restricted the use of superconductivity in high-end computing in the past. The present disclosure details several technical advances beyond the prior art, which permit development a cryogenic superconducting computing demonstrator system and ultimately energy-efficient data centers and a new generation of supercomputers.

SUMMARY OF THE INVENTION

I. Superconducting Energy-Efficient Wave-Pipelined Digital Processor

One embodiment of the technology comprises an energy-efficient superconducting microprocessor architecture, comprising integrated components as shown in a block diagram in FIG. 1. These include the arithmetic logic unit (ALU) and on-chip memory (register file). Both devices are bit-scalable and designed for an N-bit word; advanced modern microprocessors are typically configured for 64 bits. Each of these bits may be processed in parallel through both the ALU and the register file, but there are also carry-bit signals that propagate from less significant bits to more significant bits. The most conservative approach would be to process each of the N bits at the clock rate for a given operation before transferring the N-bit word to the next stage. However, this would require a long N-bit delay for the carry bit to propagate from the Least Significant Bit (LSB) to the Most Significant Bit (MSB). Even for the ultrafast clock rates $f_{cl}$ of RSFQ circuits that approach or exceed 100 GHz, a fully synchronous delay period of $N/f_{cl}$ would slow down the processor to an unacceptable degree.

In a preferred embodiment with a wave pipelined approach, the carry signal is asynchronous and propagates at maximum speed across the N bits of the ALU. According to this approach, a pipeline stage is allowed to start its operation on two independent data operands as soon as both operands arrive. There is no clock pulse used to advance the computation from one stage to another. Instead, a clock pulse that follows the data is used to reset the cells in a given stage to make them ready to process the next data wave. This type of synchronization is distinct from an earlier RSFQ-based pipelined ripple-carry adder, where a co-flow timing technique was used to clock data throughout the entire adder requiring a clock distribution tree for every stage. The present wave pipelined ALU architecture (FIG. 1) exploits the advantages of local timing in an ERSFQ ALU, by propagating an instruction code and a clock signal together from LSB to MSB of the operands. These "skewed words" (corresponding to the tilted lines in FIG. 1) propagate through the ALU, and continue on to the memory register below, providing extremely high data throughput.

A prototype 8-bit ERSFQ ALU was designed and simulated, and for a 44 GHz clock rate, provided a throughput of 350 Gbit-ops/s. Taking the switching energy to be $I_C\Phi_0$, and estimating $I_C$=40 µA, gives the energy performance as $2.5\times10^{17}$ bit-ops/J, a remarkably efficient number. One can also take the reciprocal of this to obtain the energy/bit-op, which is $4\times10^{-18}$ J, much smaller than that for classical RSFQ circuits, and orders of magnitude smaller than that for the most advanced semiconductor processors. By virtue of the modular architecture, this estimate should be independent of the size of the word, and should continue to apply for an advanced 64-bit processor.

In another aspect of a preferred embodiment of the energy-efficient processor, the register file is also scaled up not only in word size (number of bits per register), but also in the number of registers it contains. For example, a reasonable number of registers for an advanced 64-bit processor may be 128. This would correspond to a register file that can store and manipulate 64×128=8192 bits (1 Kbyte). As is known in the prior art, energy-efficient RSFQ circuits are naturally biased in parallel with a very small average voltage $V=\Phi_0 f_{cl}$, where $\Phi_0$=h/2e=2 µV/GHz and the clock frequency may be as high as $f_{cl}$=100 GHz. Such a small voltage ~200 µV is inconveniently small for an energy-efficient power supply. The bias current per Josephson junction is ~0.1 mA, which for a chip with 100,000 junctions would lead to a total bias current ~100 A, which may be inconveniently large. One way to address this mismatch is the use of serial biasing of repetitive modular circuits, also known in the prior art as "current recycling". See, for example, S. Kaplan, "Serial biasing of 16 modular circuits at 50 Gb/s", IEEE Trans. Appl. Supercond., vol. 22, 1300103 (August 2012), expressly incorporated herein by reference. This approach increases the total voltage and decreases the current by the number of modular units serially biased. In a preferred embodiment of the register file, each of the 128 registers may be designed on a separate section of ground plane, allowing the registers to be serially biased (see FIG. 2).

The modular nature of this preferred architecture has a number of advantages which simplify scaling to larger systems. From a design perspective, the scaling of the processor can proceed from a word size as small as 1 bit, and any problems related to system scale such as global timing, performance margins, and fabrication yield will manifest themselves incrementally, so that they can be isolated and solved efficiently. The register file is similarly modular, making it possible to integrate the processor with the register file in an efficient manner, starting at a word size of two bits. This enables the skewed word high-speed wave-pipelined datapath initiated in the ALU to continue unimpeded into the register file (see FIG. 1), which requires coupling across many DC isolation steps associated with the serial DC biasing.

II. High-Inductance Wiring Layer for Energy-Efficient RSFQ Circuits

Another embodiment of the invention will incorporate superconducting inductive elements formed from a high-inductance wiring layer into the design of energy-efficient RSFQ circuits. All superconductive connecting wires exhibit inductance, since the resistance is zero or negligible. In RSFQ circuits of the prior art, the inductance is desired to be small in many connecting wires, while larger values of inductance are desired in some connections. In energy-efficient RSFQ designs, large inductances may be required for current distribution in power bias lines, since the more conventional bias resistors, which produce static power dissipation, are removed. Furthermore, relatively large inductors are needed in all RSFQ designs for "quantizing loops" in bistable elements such as latches, switches, registers, and memory cells. See FIG. 3 which shows an example energy-efficient RSFQ circuit with inductors labeled that might be patterned from a high-inductance wiring layer. Specifically, the loop inductance in such a quantizing loop is typically given by $LI_C\sim\Phi_0$=h/2e=2 mA-pH. Taking a typical $I_C\sim$0.1 mA, one needs L~20 pH. Note that high-permeability magnetic materials may not be used with such superconducting inductors given the need to carry ps pulses, so that the conventional magnetic inductance is given approximately by $L\sim\mu_0 a$, where a is a characteristic dimension (such as a length or loop diameter) and $\mu_0$=1.26 µH/m=1.26 pH/um is the permeability of free space. Note that L~20 pH corresponds to a~20 µm, which is not a small size for high-density integrated circuits. While there are certainly known methods to increase inductance (such as multi-turn coils), large magnetic inductors may have other disadvantages for RSFQ circuits, associated with unintended mutual inductive coupling to other inductors in the circuit and to trapped magnetic flux (vortices) that may also be present in nearby locations on the chip.

In a preferred embodiment of the technology, the circuit comprises at least two distinct wiring layers, one with low inductance and another with high inductance. The high-inductance wiring layer may exhibit substantially enhanced values of inductance based on the property known in the art as kinetic inductance, whereby most of the effective inductance is associated not with magnetic fields external to the conductor (corresponding to conventional magnetic inductance), but rather with kinetic energy of the current-carrying electrons inside the conductor. The kinetic inductance does not couple magnetic fields, but is otherwise equivalent to circuit inductance (V=L dI/dt) for most other purposes. See, for example, U.S. Pat. No. 4,028,714, expressly incorporated herein by reference; also see en.wikipedia.org/wiki/Kinetic_inductance; Chen et al., "Kinetic Inductance Memory Cell", IEEE Trans. Appl. Supercond., vol. 2, p. 95 (1992); Johnson et al., "Anomalous current dependence of kinetic inductance of ultrathin NbN meander lines", IEEE Trans. Appl. Supercond., vol. 7, p, 3492 (1997). Any superconducting inductor will comprise both magnetic inductance and kinetic inductance; however, most superconducting inductors in the prior art, particularly those associated with RSFQ circuits, were comprised predominantly of magnetic inductance. In contrast, the high-inductance wiring layer of a preferred embodiment may exhibit an inductance which is comprised predominantly of kinetic inductance. Such an inductor is not constrained by the conventional magnetic relation $L \sim \mu_0 a$, and can have a large inductance in a very small length, enabling increased device density in integrated circuits. Furthermore, the use of inductors dominated by kinetic inductance may reduce the negative effects of parasitic inductive coupling between signals on different connecting lines and with trapped flux.

In a further preferred embodiment, the high-inductance wiring layer dominated by kinetic inductance may comprise a thin superconducting layer of a different superconducting material than that of the low-inductance wiring layer. For example, the low-inductance wiring layer may be comprised of niobium (Nb), while the high-inductance wiring layer may be comprised of niobium nitride (NbN). Furthermore, the high-inductance wiring layer may comprise a very thin layer of NbN, with a thickness $t \ll \lambda$, where $\lambda$ is the magnetic penetration depth of the superconductor. In this limit, the kinetic inductance per square of the film is given by a surface inductance $L_s = \mu_0 \lambda^2 / t$, where $L = L_s$ (l/w) for a line of length l and width w. (See later Detailed Description and FIG. 23B.) For example, taking typical values $\lambda \sim 500$ nm (for NbN) and $t \sim 50$ nm gives $L_s \sim 6$ pH. With such a high-inductive layer, it is easy to construct a quantizing inductance $\sim 20$ pH using l/w$\sim$3 squares.

In prior art RSFQ processes, a typical low-inductance layer (comprised of Nb) might exhibit an inductance per square less than $\sim 1$ pH. One can certainly construct an inductance $\sim 20$ pH with such a layer, but it will not be compact. It is important to appreciate that a high-inductance layer cannot properly be used for general connection of Josephson devices in RSFQ circuits, because such a connection would lead to unintended bistable quantizing loops where none were intended. So a practical RSFQ circuit can take advantage of such a high-inductive layer only if there is at least one other low-inductance layer available. Such a combination of both a low-inductance layer and a high-inductance layer has not been available in the design of prior art RSFQ circuits. The preferred examples of Nb and thin NbN layers, appropriately separated by insulating layers (such as $SiO_2$), are fully compatible and easily combined in an integrated multilayer process (see, e.g., U.S. Pat. No. 5,962,865, expressly incorporated herein by reference).

A further advantage of a high-inductance layer is that it can be used to restrict propagation of ps pulses on DC bias lines. In RSFQ circuits, a superconducting ground plane is used for shielding of electrical and magnetic signals from different parts of the circuit. In this case, all superconducting interconnects and bias lines are effectively low-loss microstrip transmission lines. Such passive transmission lines are used for transporting signals between different parts of the circuit at high speeds, but bias lines used for DC power distribution should not propagate these signals. In conventional RSFQ circuits, resistors can be inserted to block such pulses, but they will also dissipate power. In energy-efficient RSFQ circuits, such resistors are avoided. Instead, one can insert a short section of an inductive line with a sharply different characteristic impedance for ps pulses, which creates a mismatch that restricts pulse propagation. Such a mismatch can be easily designed using a short length of a high-inductance layer of the present technology.

III. Hybrid Superconducting-Magnetic Memories Based on Magnetic Josephson Junctions The most natural hybrid superconducting-magnetic memory technology is one that builds the magnetic memory element right into the basic superconducting component, the Josephson junction. Such a magnetic Josephson junction (MJJ) has recently been developed in the prior art (see, e.g., US Patents 2012/0184445; 2012/0302446; expressly incorporated herein by reference), but its integration with energy-efficient RSFQ technology for large magnetic random access memories (MRAMs) is still being refined. Such a hybrid integrated MRAM may be called SPEED-MRAM, for SuPerconducting Energy-Efficient Dense MRAM. Several preferred embodiments of SPEED-MRAM are disclosed below.

First, several alternative MJJ vertical stacks are considered (see FIG. 4). These are known as SIsFS, SIsFsFS, and SFIFS, where an SIS stack (superconducting/insulating/superconducting tunnel junction) is a conventional Josephson junction. Here S represents a strong superconductor such as Nb, I represents a thin insulator such as 1-2 nm of $Al_2O_3$, F represents a thin ferromagnetic layer, such as Ni, or Pd with 1% Fe (denoted in FIG. 3 as PdFe) that is ferromagnetic at cryogenic temperatures. Small s represents a weak superconductor, such as an ultrathin layer of Nb strongly coupled to an F layer. FIGS. 5A and 5B shows a prototype SIsFS MJJ switched repeatedly back and forth between the zero-voltage and the finite voltages states using an external weak magnetic field (see T. Larkin, et al., "Ferromagnetic Josephson switching device with high characteristic voltage", Appl. Physics Letters, vol. 100, 222601, May 2012). This is not an optimized fast-switching memory cell (note the time scale of seconds), but illustrates the basic principles. Based on these preliminary results, one can project that this device is scalable down to submicron dimensions, and is electrically and technologically compatible with RSFQ circuits. Specifically, the MJJ switching voltage $\sim 0.5$ mV is of the proper magnitude for reading with and writing to RSFQ circuits, and the MJJ devices can be fabricated as part of the same integrated circuit as RSFQ circuits.

Another MJJ-based structure is a three-terminal device, the superconductor-ferromagnet transistor (SFT), with a stack SFIFSIS, where each of the three superconductor layers is a separate terminal (see FIG. 7A-7C). Here the SIS junction is a Josephson junction, and the SFIFS junction serves as an injector to switch the Josephson junction on and off. (See, G. Prokopenko, et al., "DC and RF measurements of superconducting ferromagnetic multiterminal devices", Proc. 2013 IEEE International Superconductive Electronics Conf., expressly incorporated herein by reference). This is analogous to a semiconductor transistor, and shows a similar isolation between input and output. This provides the basis for an MJJ cell selector.

Another embodiment of the invention comprises an MJJ memory array, with RSFQ write and readout. These enable an MRAM with ultra-small cell area, defined only by the small MJJ size (which can be deep submicron), and energy dissipated only during Write and Read '1' operations. Only simple line drivers are required for Write and Read operations. Furthermore, the switching time of an MJJ is ~1 ps with a switching energy ~0.1 aJ, comparable to those of a conventional SIS Josephson junction employed in low-power SFQ circuits. This enables MJJs to be used as programmable Josephson junctions, a new feature in superconducting electronics not previously available. Two alternative preferred readout designs are presented, both leading to extremely energy-efficient, small-area, fast memory cells suitable for dense, scalable MRAM designs. These are applicable for cache, main memory, and possibly even for multi-port register files. The first design (FIGS. 7A-7C, see also FIGS. 25A-25B and later detailed description) is a single MJJ with a ballistic SFQ readout (SFQ-MJJ). The second design (FIGS. 8A-8C) follows a somewhat more conventional MRAM approach with a single-MJJ cell combined with a three-terminal SFT cell selector (SFT-MJJ). This is also described in more detail below. (In some cases, an alternative three-terminal nanowire superconducting device, described below, may be substituted for the SFT.)

A preferred embodiment of an MJJ memory array may further comprise MRAM periphery circuits, such as an address decoder and a bit-line driver, all implemented using energy-efficient RSFQ logic. These are described in greater detail in the Detailed Description section below.

IV. Superconducting Interface Circuits for Spintronic Memory Cells

A completely different type of magnetic memory cell is referred to as spintronic, which may comprise a magnetic material with an electronic spin-transfer property. Two such properties are orthogonal spin transfer (OST) and spin-Hall effect (SHE). MRAM arrays based on these effects are being developed for semiconductor I/O at room temperature. See, e.g., US Pub. Apps. 2012/0294078; 2014/0015074; 2014/0001524; see also, WO 2013/025994, all expressly incorporated herein by reference. However, in the present application, a preferred embodiment of the invention shows how similar cells optimized for cryogenic temperatures (see, e.g., L. Ye et al., "Spin-transfer switching of orthogonal spin-valve devices at cryogenic temperatures", J. Applied Physics, vol. 115, 17C725 (2014)) may alternatively be used as part of a hybrid superconducting-magnetic memory scheme, where low-power superconducting SFQ circuits are used to interface these cryogenic OST (COST) and cryogenic SHE (CSHE) cells.

These spintronic cells may not be directly compatible with Josephson junctions (e.g., due to higher impedance levels for the OST and SHE devices), so superconductor adaptor circuits may be used for readout and selection. In one preferred embodiment, a memory cell comprises a COST junction connected in parallel with an unshunted SQUID via an inductance (see FIGS. 9A-9B), in a configuration known as a Relaxation Oscillator (RO). The operation of this cell is described further below. One drawback of this RO-SQUID COST cell is the relatively large device area (as large as 100 μm$^2$) due to the use of two Josephson junctions and inductors.

Two other preferred embodiments (which may be much smaller) make use of a superconducting three-terminal device for readout and selection. The superconductor NanoWire Device (NWD), also known as the Nano-Cryotron or nTron, is essentially a superconductor transistor comprising a narrow superconducting channel (width less than 100 nm) modulated by injection current from a superconducting gate (see FIG. 10). See A. McCaughan and K. Berggren, "A Superconducting Nanowire Three-Terminal Electrothermal Device", Nano Letters, vol. 14, no. 10, pp. 5748-5753 (September 2014), expressly incorporated herein by reference. This structure is an improvement upon earlier prior art superconducting three-terminal devices, see, e.g., O. Quaranta, et al., "Superconductive three-terminal amplifier/discriminator", IEEE Trans. Appl. Supercond., vol. 19, p. 367 (2009). A preliminary test of this new device, fabricated from thin NbN film, was able to provide output currents of 40-80 μA to devices with impedances from 10Ω to 10 kΩ, with a 10 μA input signal, with frequency response up to ~1 GHz expected.

The NWD can be used with either COST or CSHE cells for cell selection—see cells and arrays in FIGS. 11A-11B and 12A-12B. The CSHE is a three-terminal device that allows decoupling of Read and Write operations. For a hybrid CSHE-NWD cell, the NWD is the selection element for Write operations (FIGS. 11A-11B). Read operations require a separate grid of impedance-matched lines for transmitting voltage pulses along a row, while sensing their responses along all columns, thus providing word-access memory readout.

Another preferred embodiment is a COST-NWD memory cell and array, as shown in FIGS. 12A-12B. Here, the COST is a two-terminal device, requiring a different readout scheme. The NWD selects a given cell for reading or writing. Once the NWD switches from superconducting to resistive upon activation of the Word Line Select Current (WL), it redirects the Read or Write current to the COST element. When the WL current is off, the NWD quickly returns to the superconducting state. The power is dissipated only at the selected cells during Read or Write operation. Since the NWD has a significant power gain, only a very small current is required to activate it. Furthermore, the NWD and the COST can be fabricated with closely matching impedances, much higher than that of RSFQ circuits. The NWD and COST can be fabricated side-by-side in an area less than 4 μm$^2$, corresponding to a cell density greater than 10 Mbits/cm$^2$. The cell size can be reduced even further by placing the NWD selector underneath the COST. Further operation details are presented below.

Alternatively, these spintronic memory cells may be interfaced with RSFQ circuits using the SFT, the other three-terminal superconducting device described above as an interface for the MB cells (FIG. 8).

V. Cryogenic Multi-Chip Module (MCM) for Hybrid Technology Computing System

The combination of cryogenic operation, ultra-high-speed, and ultra-low-power of the hybrid superconducting-magnetic computing devices and memory make testing difficult, and require developing a new infrastructure for interfacing these devices with conventional room-temperature digital and analog systems. For example, in order to perform a comprehensive characterization of a 64×64 SPEED-MRAM chip at full speed, one needs to construct an interface capable of sending 64-bit words, addresses, and control signals between the chip and room-temperature test instruments. FIG. 13 shows the block diagram for a preferred embodiment of such a prototype test system, comprising two main parts: a cryogenic (4 K) testbed multi-chip module (MCM), and a room-temperature FPGA-based (field-programmable gate array) memory test controller (MTC). All high-speed parallel data communications and measurements are done on the testbed MCM at 4K, while communication with the MTC occurs via slower serial links. For prior art on high-speed communication on superconducting MCMs, see U.S. Pat. Nos. 8,159,825; 6,420,895;

6,580,510, expressly incorporated herein by reference. See also, D. Gupta, et al., "High-speed inter-chip data transmission technology for superconducting multi-chip modules", IEEE Trans. Appl. Supercond., vol. 11, p. 731 (2001); S. Narayana, et al., "Design and Testing of high-speed interconnects for superconducting multi-chip modules", Supercond. Sci. Technol., Vol. 25, 105012 (2012), expressly incorporated herein by reference.

The testbed MCM comprises a superconducting Test Control and Acquisition chip (TCA), together with a hybrid memory chip that may comprise MRAM cells with superconducting interface circuits. The MRAM cells may comprise MJJ, COST or CSHE devices. The TCA chip comprises a superconducting digital processor, comprising proven RSFQ circuits including serializer/deserializer (SERDES) circuits, shift register buffers, clock controllers, a time-to-digital converter (TDC), and interchip communication circuits for 64-bit parallel words with clock recovery. A functional block diagram of the key components of the TCA is shown in FIG. 14. The TCA chip communicates at MHz rates with the MTC module, which loads and unloads 64-bit data words and addresses.

During functional operation, the testbed MCM is maintained at a cryogenic temperature, which may preferably be around 4 K. In one embodiment, the MCM may be immersed in a container of liquid helium. In a preferred embodiment, the MCM may be mounted inside a vacuum chamber and cooled by thermal conduction to a cold stage of a closed-cycle refrigerator, also known as a cryocooler. The lines between the MCM and the MTC module may comprise a plurality of digital electrical RF cables with low crosstalk and DC bias lines, both designed to minimize thermal conduction or dissipation. In one embodiment, at least one of the DC or RF lines may comprise a high-temperature superconductor which can operate as a superconductor at a temperature in excess of 20 K. In an alternative embodiment, at least one of the lines may comprise an optical communications medium, such as for example an optical fiber for communicating infrared data pulses.

Transmitting 64-bit words from chip to chip at high rates (which may range from 20 GHz to 100 GHz or more) is a very challenging task, because of timing uncertainty. In all RSFQ logic, including energy-efficient RSFQ, local timing is used, so that the problem of clock recovery is quite different than that for global timing circuits. FIG. 15A shows a preferred embodiment of a high-speed inter-chip bit-parallel communication system, comprising a clock recovery system for SFQ ballistic transmission of a parallel word over long distances. Here the multi-bit data is transmitted from a transmitting chip (Tx) on the left, to a receiving chip (Rx) on the right, over a parallel set of passive transmission lines (PTLs) on the multi-chip module. At the Tx side, the data is converted to a dual-rail form, with each bit propagating along two parallel PTLs; one for '1' and the other for '0'. At the Rx side, each '1' line goes to a buffer (First-In, First-Out or FIFO) awaiting release by a recovered clock signal. Furthermore, all of the bits on '0' and '1' lines are merged via a binary tree of Muller C-elements, shown in FIG. 15B (also known as confluence buffers, see, e.g., en.wikipedia.org/wiki/C-element; pavel.physics.sunysb.edu/RSFQ/Lib/c.html, expressly incorporated herein by reference).

The output of this tree comprises the recovered clock pulse, and ensures that the latched bits are released only when all bits have successfully arrived. This should provide a very reliable system for ultra-high-speed bit-parallel communication between superconducting chips. Further details of the circuit, implemented using energy-efficient RSFQ logic, are presented in the Detailed Descriptions section.

It is to be understood that a preferred embodiment of a system employing such a testbed MCM also provides a prototype of a larger-scale supercomputing system, which would incorporate a plurality of such chips and MCMs, communicating at high speeds. An MCM could comprise additional memory chips on the same MCM, and two or more MCMs could be mounted in close proximity on the same cryogenic stage; furthermore, a system could comprise a plurality of digital processors operating in parallel within a common cryogenic environment. Further details are discussed below.

VI. Integrated Circuit Process with Both Superconducting Circuits and MRAM Cells The prior art has disclosed multilayer IC processes for superconducting circuits, and for MRAM arrays with transistor interfaces. Here, several preferred embodiments for fabricating integrated superconducting/MRAM circuits on the same chip for cryogenic operation are disclosed.

The first preferred embodiment comprises a fabrication system and method for combining magnetic Josephson junctions (MJs), superconducting ferromagnetic transistors (SFTs), and non-magnetic Josephson junctions (JJs) together in the same chip, for fabrication of SPEED-MRAM chips (see FIGS. 16 and 17). This process builds on prior art superconducting circuit processes, and a new planarized multilayer process disclosed in a recent provisional application (D. Yohannes, et al., "Method for increasing the integration level of superconducting electronics circuits and a resulting circuit", U.S. application 61/887,919, filed Oct. 7, 2013, and Ser. No. 14/508,514, filed Oct. 7, 2014, each of which is expressly incorporated herein by reference). This process has been named "Rapid Integration of Planarized Process for Layer Extension", or RIPPLE. FIG. 17 shows a cross-sectional view of a patterned circuit that comprises both a standard SIS Josephson junction, and also an array of MJJ memory cells. FIG. 17 also shows the steps to produce both an MJJ and an SFT.

The second preferred embodiment comprises a fabrication system and method for combining COST cells and NWD devices together with more conventional superconducting circuits on the same chip. This embodiment, shown in FIG. 18, shows a chip cross section for a circuit in which NWD drivers and COST-MRAM memory cells are fabricated on top of pre-fabricated planarized Josephson junction (RSFQ) circuits. A similar fabrication process is proposed with the alternative CSHE-MRAM memory cells with NWD drivers. Further details are given below.

It is therefore an object to provide a cryogenic computing system, comprising a high-speed superconducting digital processor, configured to operate at cryogenic temperatures at a clock rate of at least 20 GHz; an array of memory cells, comprising a switchable magnetic material, configured to operate at cryogenic temperatures; and superconducting interface circuits configured to communicate between the array of memory cells and the processor, configured to operate at cryogenic temperatures.

It is also an object to provide a method for fabricating a superconducting computer, comprising designing a processor using ultrafast energy-efficient superconducting rapid-single-flux-quantum logic and memory register cells; implementing ultrafast wave-pipelining in both logic and memory; designing a cryogenic random access memory array using switchable magnetic elements (MRAM); designing superconducting interface circuits between the processor and the MRAM; fabricating at least one MRAM chip using a deposition process that incorporates both superconducting and magnetic elements on the same chip; packaging the processor and MRAM chips on at least one multi-chip module (MCM); designing and fabricating the MCM to permit ultrafast data transfer between the processor and MRAM chips; and designing and implementing a cryogenic system for maintaining the processor and the MRAM at cryogenic temperatures suitable for operation.

It is a further object to provide a superconducting computer, comprising a processor integrated circuit comprising energy-efficient superconducting rapid-single-flux-quantum logic and superconducting memory register cells, having ultrafast wave-pipelining in both the energy-efficient superconducting rapid-single-flux-quantum logic and the memory register cells; a cryogenic random access memory array integrated circuit comprising a plurality of switchable magnetic elements (MRAM), fabricated using a deposition process that incorporates both superconducting Josephson junction and magnetic elements; and at least one superconducting interface circuit disposed between the processor and the MRAM; wherein the processor integrated circuit and MRAM integrated circuit are packaged on at least one multi-chip module (MCM) configured to permit ultrafast data transfer between the processor integrated circuit and the MRAM integrated circuit. The superconducting computer may further comprise a cryogenic system configured to maintain the processor integrated circuit and the MRAM integrated circuit at cryogenic temperatures suitable for operation of superconducting digital logic elements.

It is a still further object to provide a processing method, comprising cooling a cryogenic computing system within a temperature range at which low temperature superconducting materials are superconductive, the cryogenic computing system comprising: a superconducting digital processor, an array of memory cells, comprising a switchable magnetic material, and superconducting interface circuits configured to communicate between the array of memory cells and the processor; transforming at least one digital datum by the superconducting digital processor; transferring the transformed at least one digital datum through the superconducting interface circuits; and storing the transformed at least one digital datum in the array of memory cells.

The digital processor may comprise energy-efficient rapid-single-flux-quantum logic. The digital processor may also comprise an asynchronous wave-pipelined datapath. The digital processor may also comprise a plurality of serially biased modular superconducting circuits. The digital processor further comprise superconducting inductor elements fabricated from at least two distinct superconductor wiring layers with substantially different sheet inductances.

Both the processor and the array of memory cells may be designed and configured to operate at cryogenic temperatures less than 10 K.

The sheet inductance of at least one of the wiring layers may be predominantly due to kinetic inductance.

The array of memory cells may comprise a plurality of memory cells, each comprising a Josephson junction having a Josephson junction barrier having a thin magnetic layer. The plurality of memory cells may be read out using ballistic single-flux-quantum pulses. Each memory cell of the array of memory cells may be selected using a three-terminal superconducting device. A plurality of memory cells may comprise a plurality of cryogenic orthogonal spin transfer (COST) junctions. The array of memory cells may further comprise a plurality of relaxation-oscillator SQUIDs, and wherein a respective COST junction is read out using a respective SQUID. A respective COST junction of the array of memory cells may be selected by a three-terminal superconducting device. The array of memory cells may comprise a plurality of cryogenic spin-Hall effect (CSHE) devices. Memory cells of the array of memory cells may comprise a CSHE cell selected using a three-terminal superconducting device.

The array of memory cells and the processor may comprise separate chips on respective multi-chip modules (MCMs), the cryogenic computing system further comprising a high-speed parallel communication bus between the respective MCMs. The high-speed parallel communication bus may communicate single-flux-quanta on superconducting transmission lines. The high-speed parallel communication bus may comprise a receiver having a clock recovery circuit.

The computing system may further comprise a room-temperature electronic controller, e.g., configured to control the digital processor. The digital processor and the room temperature controller may communicate via serial communications at a substantially lower rate than the parallel communication over the high speed parallel communication bus.

The digital processor and the array of memory cells may comprise integrated circuit chips, and wherein the fabrication process for the integrated circuit chips may be compatible with processing of functional superconducting and magnetic elements on the same integrated circuit chip. The digital processor and the array of memory cells may be fabricated on a common integrated circuit.

It is to be understood that these preferred embodiments represent examples of computing and memory circuits and systems of the present invention, and the invention is not restricted to these examples.

BRIEF DESCRIPTION OF THE FIGURES

FIGS. 7A-7C show a single MJJ with a ballistic SFQ readout (SFQ-MJJ), together with a schematic of a memory array.

FIGS. 8A-8C show an alternative single-MJJ cell combined with a three-terminal SFT cell selector, and a memory array of such cells.

FIGS. 19A-19B shows the schematic circuit and functional behavior of an ERSFQ half-adder cell.

FIGS. 24A-24C shows an MJJ structure with one magnetic layer (24A) an alternate MJJ structure with two magnetic layers (24B), and the electrical behavior of a corresponding junction in magnetic field (24C).

FIGS. 28A and 28B show an example of a cryogenic system on a cryocooler that may support a hybrid superconducting/magnetic memory array and digital processor. Left (28A) system overview; Right (28B) Detail of cryogenic stage including active magnetic shielding.

DETAILED DESCRIPTION OF THE PREFERRED EMBODIMENTS

I. Superconducting Energy-Efficient Wave-Pipelined Digital Processor

Figure 1:
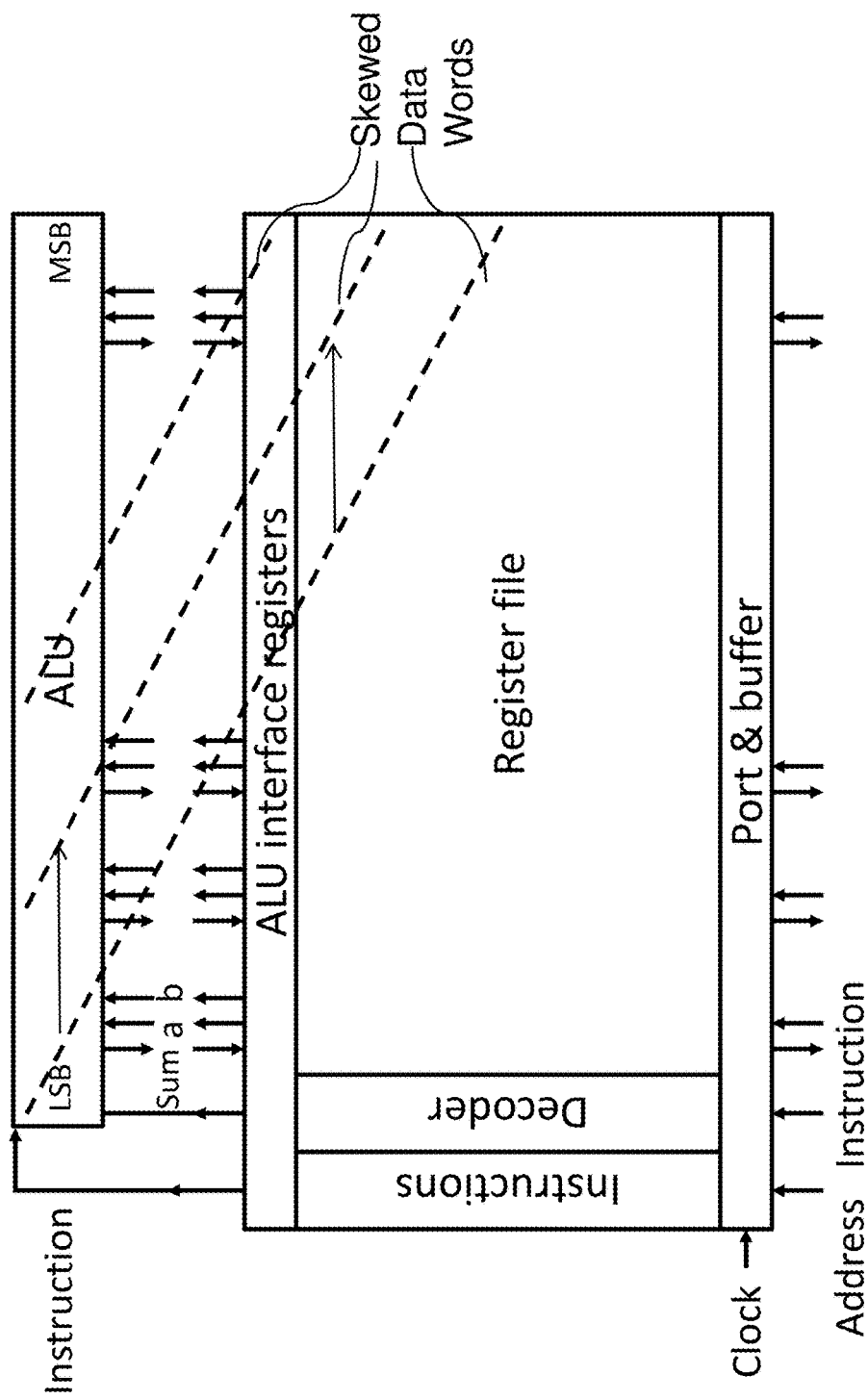
FIG. 1 shows a conceptual diagram of a high-speed energy-efficient superconducting microprocessor, comprising an arithmetic logic unit (ALU) and register file, with a wave-pipelined datapath and timing scheme exhibiting skewed words that represent asynchronous propagation of carry bits through the processor.

FIG. 1 shows a conceptual diagram of the wave-pipelined datapath and timing scheme for a proposed high-speed energy-efficient superconducting microprocessor, comprising an arithmetic logic unit (ALU) and register file, with skewed words that represent asynchronous propagation of carry bits through the processor. This multibit ALU comprises a cascade of 1-bit ALUs, and one of its unique features is that both the instruction and the carry bit cascade asynchronously through the ALU. This architecture combines the timing advantage and modular scaling found in a ripple adder with the speed advantage of asynchronous circuitry.

Figure 2:
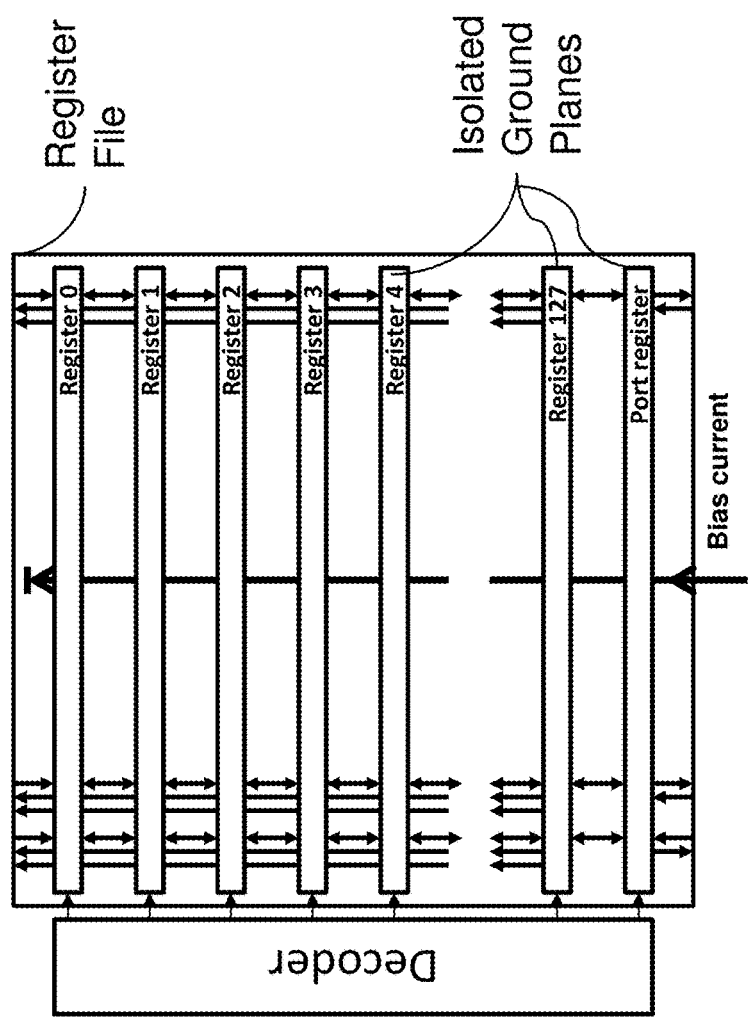
FIG. 2 shows the modular structure of the register file, with serial DC biasing of successive registers.
Figure 3:
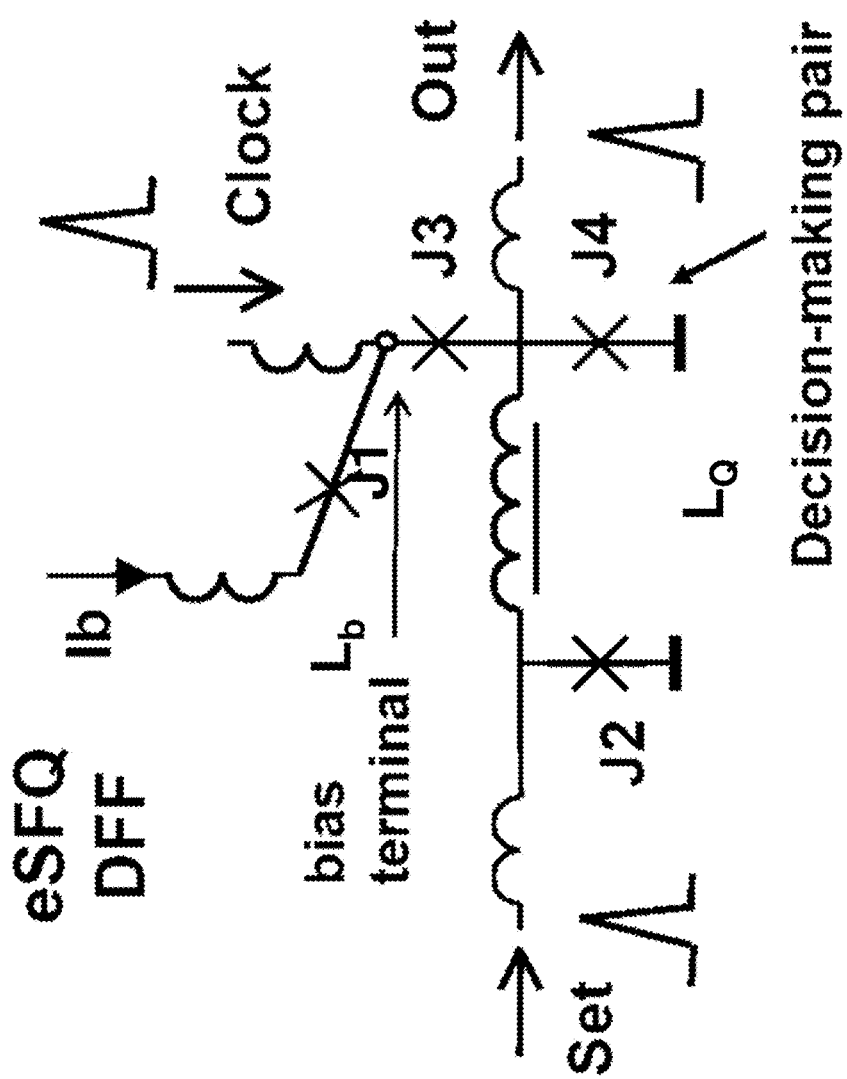
FIG. 3 shows an example energy-efficient RSFQ circuit, with bias inductor and quantizing inductor that might be fabricated from a special high-inductance superconducting layer.

A block diagram of the architecture of the register file is shown in FIG. 2. This consists of an array of 128 registers, each with an identical modular structure, designed for a 64-bit word. Since the bias current for each of these is the same, this enables the current bias for each register to be supplied in series from one to the next, known as "current recycling". The bias current for each register enters through a power line and drains to the ground plane, so this requires that the ground plane for a given register be connected through a via to the power line of the succeeding register. In addition to reducing the total bias current for the register file by the factor of 128, this scheme decouples the phases of each register's ERSFQ bias line, so that only the accessed register will dissipate power, thus also reducing the total power by the factor of 128. Note also that SFQ pulses may freely traverse from one register to the next, despite the offset in DC voltage.

Figure 19B:
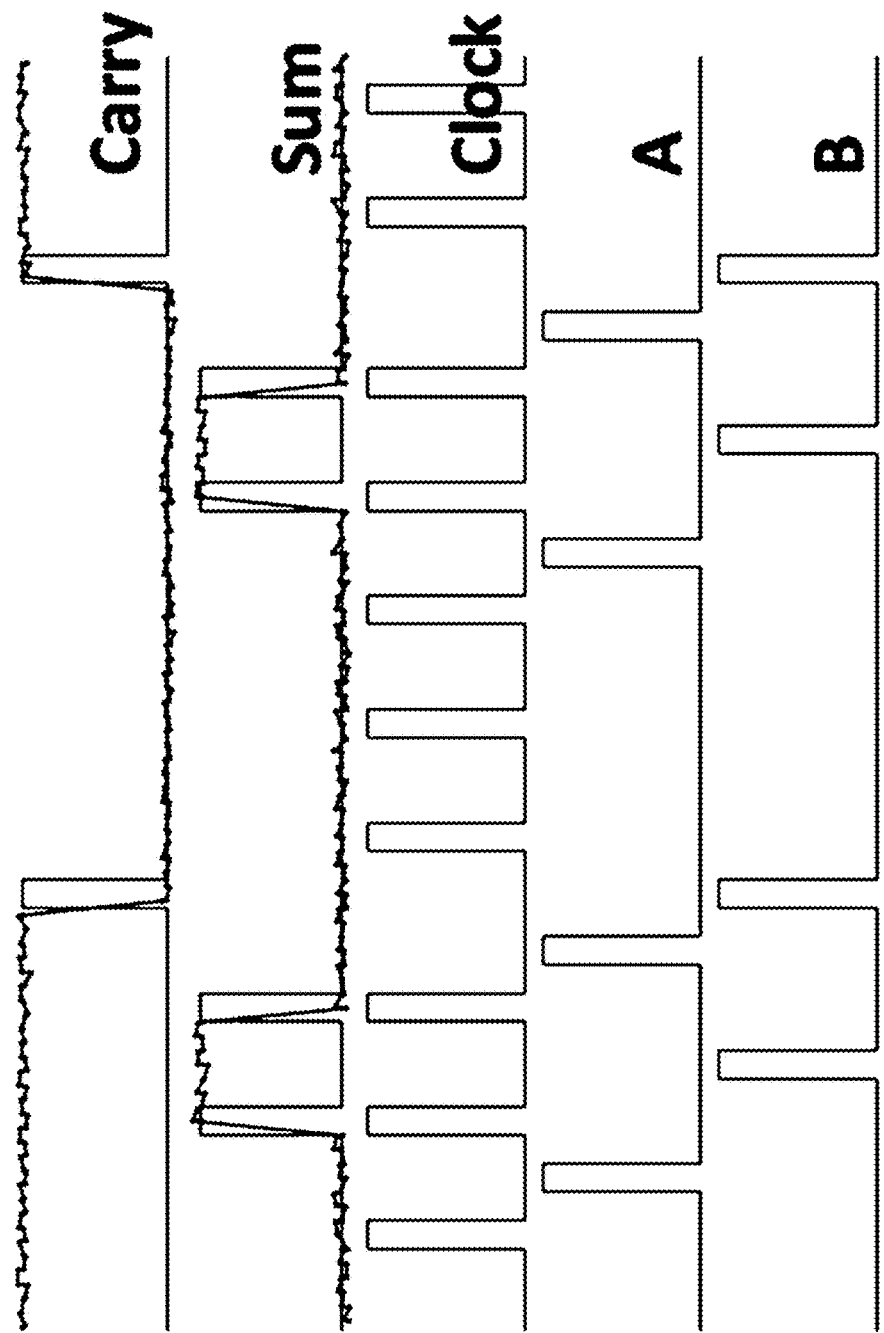

The basic element of the ALU is an ERSFQ half-adder cell (see FIGS. 19A-19B). Here the addend bits A and B are added, together with the Carry bit. The output is triggered by the arrival of the Clock pulse, generating the Sum output at the bottom. A key feature of this cell is its asynchronous Carry signal, which is not latched to a clock signal, and is therefore produced as soon as both '1' arguments arrive at the ALU. This property allows Carry signals to propagate in the form of a wave (wave-pipelining).

Figure 20:
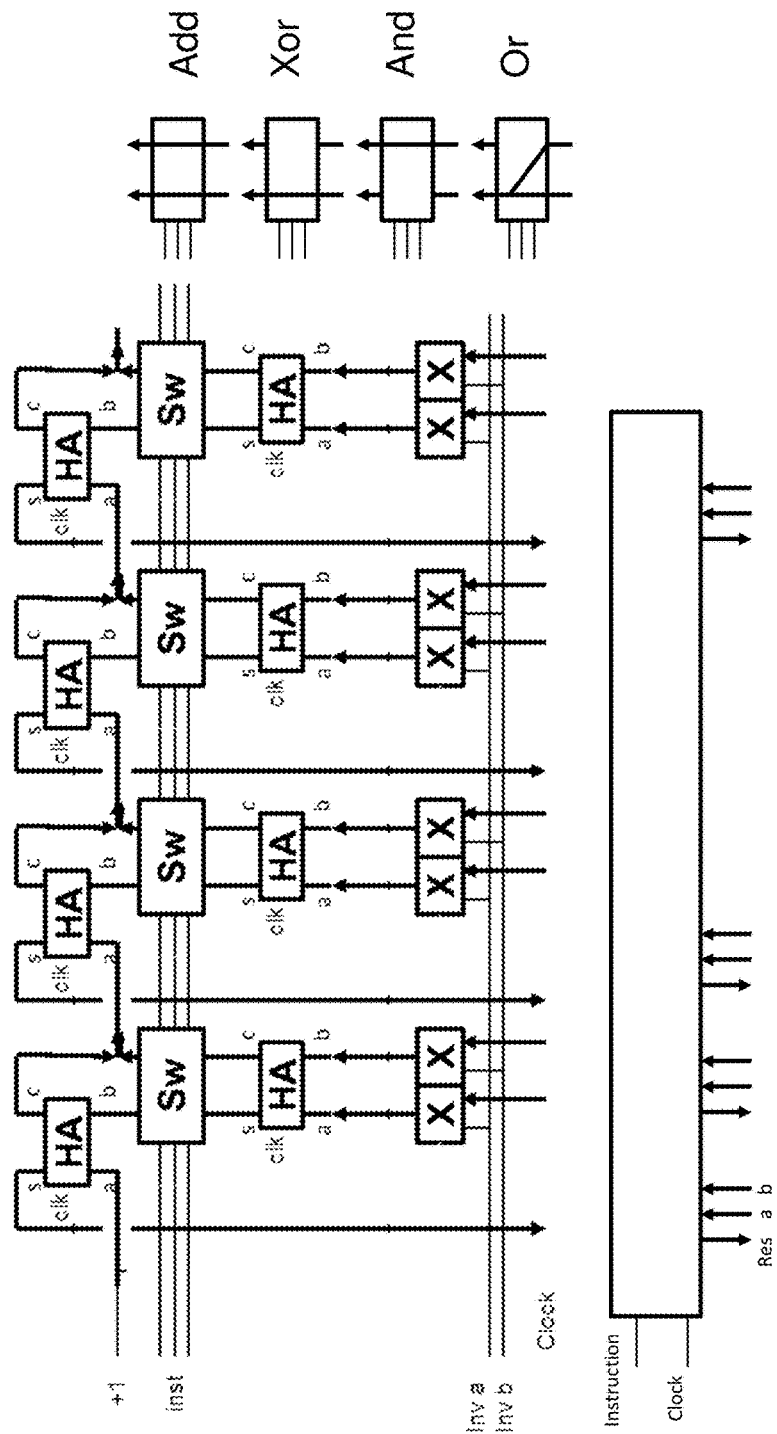
FIG. 20 shows the block diagram of an energy-efficient ALU.

A portion of the detailed block diagram of the 8-bit energy efficient ALU is shown in FIG. 20, comprising repeated half-adder units (HA). The instruction select is implemented through a switch cell (Sw) that relays Sum and Carry signals from the first stage Half Adder to the second stage, and provides for executions of such instructions as ADD, XOR, AND, and OR. In combination with selective inversion of the operands, this results in a broad instruction list. This novel ALU architecture exploits the advantages of local timing in an ERSFQ ALU by propagating an instruction code and a clock signal together from LSB to MSB of the operands.

This same "skewed word" approach (see FIG. 1) is used in reading from and writing to a register file as well, providing extremely high throughput. The short vertical dimension of the ALU provides a very low latency (~80 ps in simulation), where latency is defined as the "turnaround time" between the start of loading the LSBs of the operands, and receiving an output LSB. The wave propagation time from LSB to MSB is simulated to be ~400 ps for the 8-bit ALU, but this does not affect the performance of the wave-pipelined datapath.

Both the throughput and the energy performance of this ALU are orders of magnitude superior to ALUs in other technologies. For example, an 8-bit version of the ALU based on current fabrication technology (not fully optimized) was simulated on a circuit level, and found to operate at a clock frequency of 44 GHz, giving a throughput of $3.5 \times 10^{11}$ bit-ops/sec. The bias current drawn by a one-bit slice of this design is 50 $I_{Cmin}$, where $I_{Cmin}$ is the critical current of the smallest Josephson junction in the design. Taking the switching energy to be $I_C \Phi_0$ and using a minimum $I_{Cmin}=38$ µA gives $2.5 \times 10^{17}$ bit-ops/Joule as the energy performance of this ALU. By virtue of the modular architecture, the speed and energy per bit are independent of the word size, enabling scaling to 64 bits.

Figures 21A, 21B:
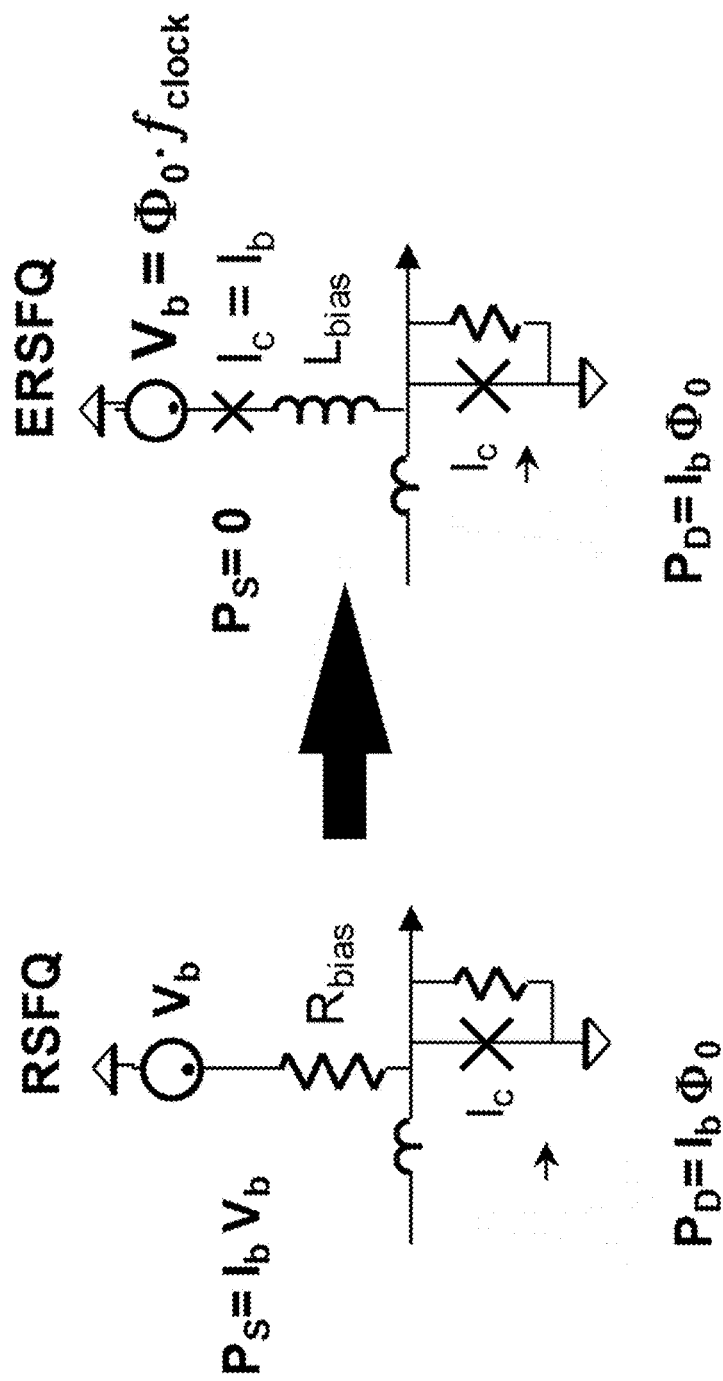
FIGS. 21A and 21B show how a simple RSFQ circuit (21A) is modified to become an energy-efficient ERSFQ circuit (21B) with zero static power dissipation.

FIGS. 21A-21B shows how a simple RSFQ circuit (a unit of a Josephson transmission line or JTL) on the left transforms to an energy-efficient ERSFQ design on the right. The junction switching dynamics (with SFQ switching energy $\sim I_b \Phi_0$) and dynamic power dissipation are the same in both cases. The only difference is that the static power dissipation $P_S$ in the bias line is eliminated by replacing the bias resistor $R_{bias}$ by a series combination of a Josephson junction (with critical current $I_c = I_b$) and an inductance $L_{bias}$. This enables the bias voltage to be reduced by a factor ~50, reducing the system power dissipation by a similar factor. Switching of the current-limiting bias junction will compensate for imbalance of average voltages across different bias terminals. Standard RSFQ cells which have already been developed can be modified to ERSFQ circuits by this simple resistor replacement.

Figures 22A, 22B:
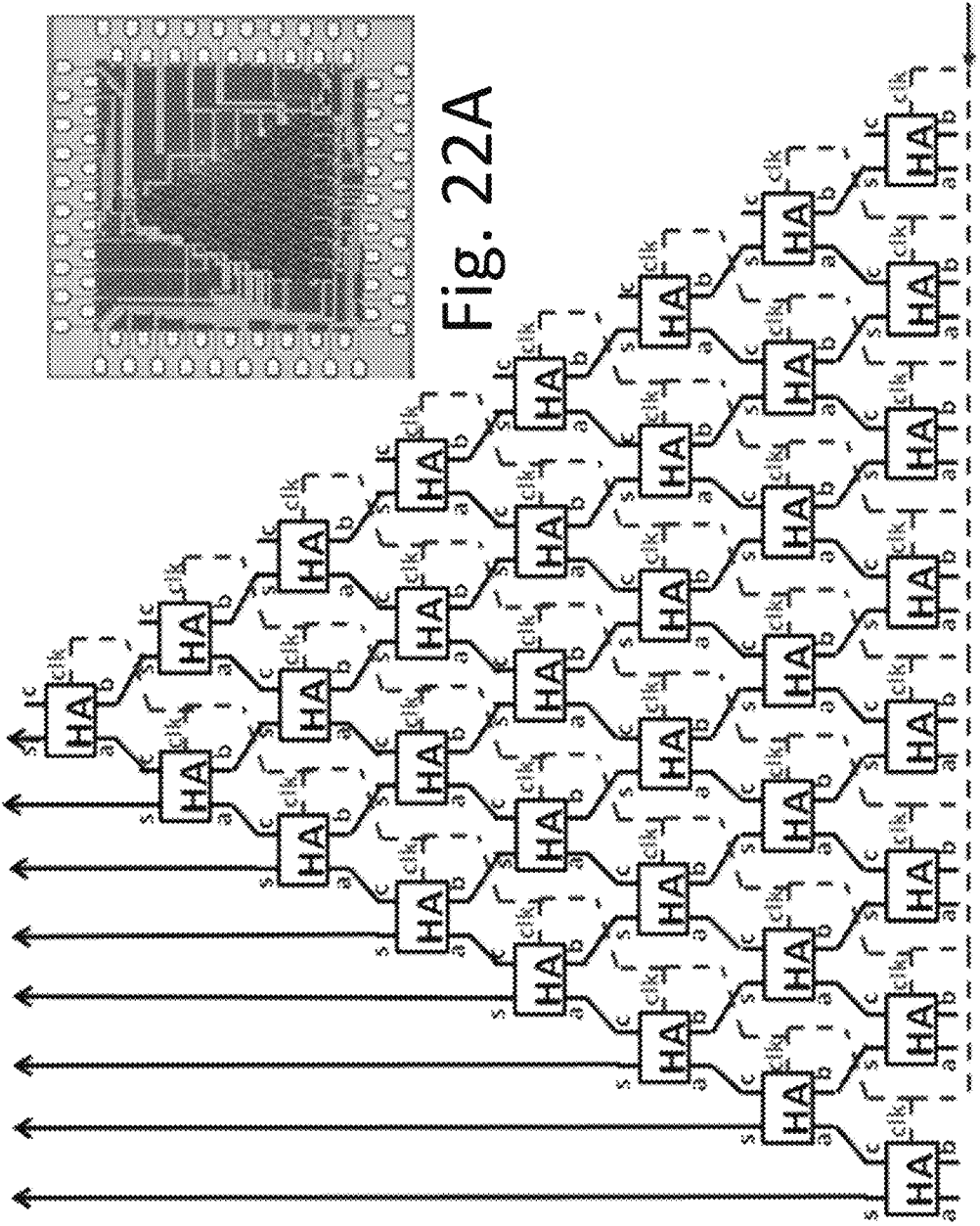
FIGS. 22A and 22B show the circuit layout and block diagram of an ERSFQ-8-bit wave-pipelined adder.

FIGS. 22A and 22B show the circuit layout and block diagram of a prototype ERSFQ 8-bit wave-pipelined adder. This is comprised of multiple identical half-adder modules of FIG. 18 (symbolized by HA in the schematic) connected in a tree structure as shown. This comprises ~2000 Josephson junctions, and this prototype operated at a clock frequency of 20 GHz with a dissipation of 0.36 fJ per operation, proving the viability of this wave-pipelined, low-power approach for larger and faster superconducting processors.

II. High-Inductance Wiring Layer for Energy-Efficient RSFQ Circuits

RSFQ electronics deals with the storage and transfer of magnetic single flux quanta (SFQ) with flux $\varphi_0 = 2$ mV-ps $= 2$ mA-pH. A loop comprising two Josephson junctions and an inductor L can store a flux quantum if $LI_C \sim \Phi_0$, where $I_C$ is the critical current of the Josephson junctions. In transporting an SFQ from one portion of the circuit to another, it is critical that the SFQ not be trapped in unintended inductors, so that normally $LI_C \ll \Phi_0$. In contrast, some loops are designed as storage elements, in which case we want a quantizing inductance $L_q = \varphi_0 / I_C \sim 20$ pH if $I_C \sim 0.1$ mA.

Figures 23A, 23B:
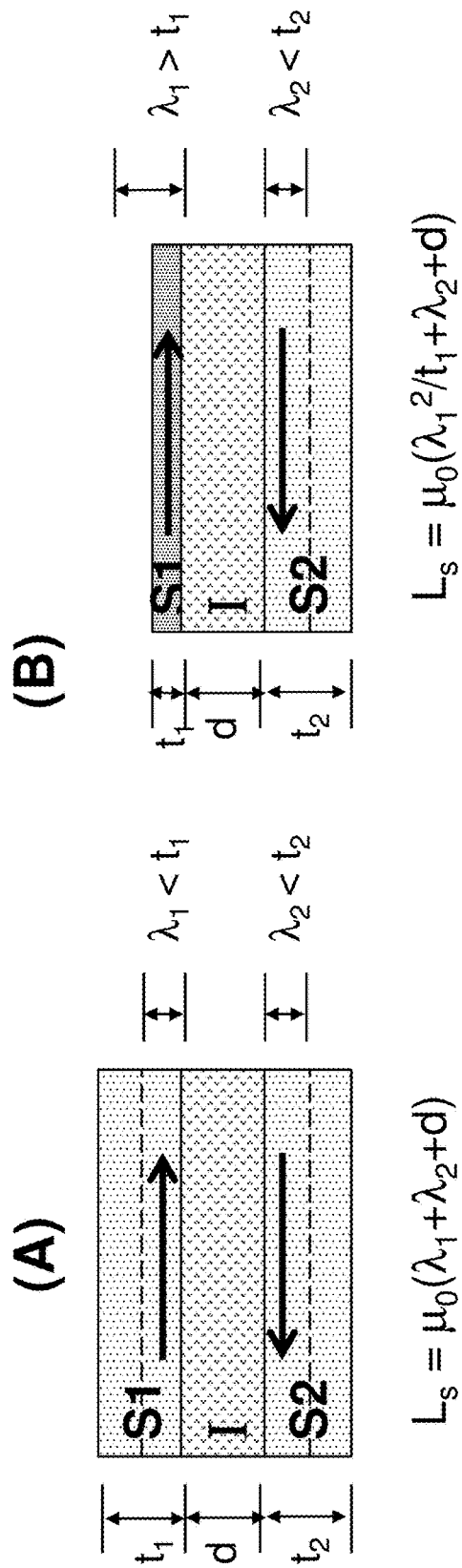
FIGS. 23A and 23B show a cross section of a superconducting multilayer process with a low inductance that is predominantly magnetic inductance (23A, left) and an alternative process with a high-inductance top layer that is predominantly kinetic inductance (23B, right).

FIG. 23A (left) shows the cross-section of a typical superconducting connecting layer above a superconducting ground plane in an integrated circuit process, where we assume that both superconductors comprise Nb, which has the highest critical temperature (9.2 K) of any simple elemental metal, and operates well at 4-5 K. Each film may be t~200 nm thick, and they are separated by an insulator (such as $SiO_2$) of thickness d~200 nm. The magnetic penetration depth $\lambda$ of Nb is ~100 nm; this is the thickness on the surface of a superconductor in which the currents flow. Consider the inductance of a parallel-plane structure of length l and width w, where we assume that w>>d so that edge effects may be neglected. Then the inductance can be given as $L = (l/w) L_s$, where $L_s = \mu_0 (\lambda_1 + \lambda_2 + d)$ is the sheet inductance or inductance per square of the line. Here $\lambda_1$ is the penetration depth of the top superconductor and $\lambda_2$ that of the bottom superconductor. The magnetic field produced by the current lies in the insulator, and penetrates into the superconductor within $\lambda$ of the surface. The contribution $\mu_0 d$ to $L_s$ is purely magnetic inductance, while the contributions $\mu_0 \lambda$ corresponding to the superconducting films (much thicker than $\lambda$) are half magnetic and half kinetic inductance. In the example here, $L_s = 0.5$ pH/square, of which about 75% is magnetic inductance and 25% kinetic inductance. Taking $I_C \sim 0.1$ mA, the quantizing inductance would be $L_q \sim 20$ pH. Short lengths of the line will have $L \ll L_q$, so that it is easy to lay out non-quantizing loops. Quantizing loops, however, will tend to be long. In prior art superconducting integrated circuits, there may be two or more superconductor wiring layers, each separated by insulators of various thicknesses. Various combinations of these layers will lead to different values of $L_s$, but they are all fairly small and predominantly magnetic.

In contrast, consider the cross-section in FIG. 23B (right), where the top superconductor wiring layer now comprises a thin film with thickness $t \ll \lambda$. In this limit, the sheet inductance due to this top superconductor is given by $\mu_0 \lambda^2 / t$, virtually all of its kinetic, and the current flows uniformly within the film. The total sheet inductance is then $L_s = \mu_0 (\lambda_1^2 / t_1 + \lambda_2 + d)$. If this top film is made from NbN with $\lambda_1 = 500$ nm (depending on deposition conditions) and take $t_1 = 50$ nm, then $L_s \sim 6.7$ pH, of which 95% is kinetic and 5% magnetic inductance. Furthermore, this thin top layer will also be able to carry a sufficiently large superconducting current at 4 K, since the superconducting critical temperature of NbN is somewhat higher than that of Nb (10-15 K, depending on deposition conditions). An inductor made with this layer will be ideal for designing a compact quantizing inductor $L_q$, as well as a compact bias inductor $L_b$, which may have a value that is comparable or larger than this quantizing inductor.

A further advantage of the use of an inductor that is primarily kinetic inductance is that it will have substantially reduced magnetic mutual inductance with other lines and with external fields, as compared with a predominantly magnetic inductance of the same value. This is particularly important for energy-efficient RSFQ, where the bias current in a given line is set by an inductor (rather than by a resistor as with conventional RSFQ), and parasitic mutual inductance may alter the bias current.

A further aspect of the availability of a high-inductance layer is that one may design a passive transmission line (PTL) with a higher characteristic impedance $Z_0$ for the same dimensions. Since $Z_0 = (L/C)^{1/2}$, increasing L by a factor of 13 increases $Z_0$ by a factor of 3.5. This may offer additional flexibility in design of PTLs, which are used in energy-efficient RSFQ to transport signals over significant distances on chip with negligible dissipation. Further, one can take advantage of such a difference in $Z_0$ to deliberately introduce a mismatch that prevents launching of a pulse on a PTL. For example, bias lines are essentially PTLs, but in conventional RSFQ, a bias resistor near the bias current insertion point acts to block the launching of an SFQ pulse onto the bias line (see FIG. 21A). In contrast, in energy-efficient RSFQ, a bias inductor is used instead of a bias resistor. If a compact bias inductor is also located near the bias current insertion point (see FIG. 21B), the impedance mismatch can also act to block the SFQ pulse from being launched onto the bias line. This may help to avoid possible crosstalk via bias line coupling.

A further advantage to a high-inductance layer is that it may be used to construct other superconducting devices that may be integrated with RSFQ digital circuits. For example, a superconducting nanowire single photon detector (SNSPD, also called SSPD or SNAP) is typically constructed from a thin NbN layer with a very high sheet inductance. See D. Gupta, "Single photon counting hotspot detector with integrated RSFQ readout electronics," IEEE Trans. Appl. Supercond., vol. 9, p. 4487 (1999), expressly incorporated herein by reference; see also U.S. Pat. Nos. 6,812,464; 7,049,593; 8,565,844; 2012/0077689; 2013/0143744, expressly incorporated herein by reference. Further, a similar NbN layer may be used to construct a three-terminal NanoWireDevice (FIGS. 9A and 9B), which operates as a transistor and may be used as cell selector for spintronic memory cells interfaced with RSFQ circuits (FIGS. 10A, 10B and 11A-11B). The availability of such a layer permits these and other essentially analog devices to be closely integrated with RSFQ digital circuits.

III. Hybrid Superconducting-Magnetic Memories Based on Magnetic Josephson Junctions One preferred embodiment comprises a class of hybrid superconducting-magnetic memories based on magnetic Josephson junctions (MJJ) and superconductor-ferromagnetic transistors (SFT). This memory technology has been called "SPEED-MRAM", for SuPerconducting Energy-Efficient Dense MRAM. For its Read and Write functions, SPEED-MRAM comprises memory cells that are integrated with eSFQ or ERSFQ energy-efficient peripheral circuitry. To fabricate SPEED-MRAM, a new fabrication process integrates MJJs, SFTs, and SFQ digital processor circuits and periphery circuits in the same fabrication cycle.

SPEED-MRAM is dense, scalable, and operates at high speed. A memory cell consists of a single small MJJ, with optional cell selector, so that density scales with the microfabrication technology. There are no poorly scalable elements, such as SQUIDs. Furthermore, SPEED-MRAM is architecturally compatible with SFQ technology, since signal levels and impedances are similar. Finally, SPEED-MRAM is energy-efficient; the Read operation is performed with an SFQ pulse, and consumes energy only when '1' is read out. A low Write energy is achieved by employing a magnetic junction barrier that is a soft magnetic material with a low coercivity. Periphery circuits are realized with energy-efficient SFQ logic.

A preferred memory element in SPEED-MRAM comprises a magnetic Josephson junction (MJJ) that is comprised of vertical stacks of superconducting, magnetic, and insulating layers (S, F, and I), such that there is a superconducting critical current $I_C$ that is ~0.1-0.5 mA (or even smaller), and a normal-state junction resistance $R_n$ such that $I_C R_n$~0.5 mV, similar to that of Josephson junctions in conventional RSFQ. Since $\Phi_0$=2 mV-ps, the switching speed is ~4 ps. Preferred stacks are SIsFS, SIsFsF, and $SF_1IF_2S$ (see FIG. 4), where small s represents a very thin superconducting layer that is weakly superconducting due to the proximity of a magnetic layer. A preferred superconducting layer is Nb; a preferred I layer is a tunnel barrier $Al_2O_3$, which may be produced by oxidizing a thin layer of Al, and may be only ~1-2 nm thick. The magnetic layer is preferably ferromagnetic, with one preferred composition (which is not unique) comprising magnetically soft dilute $Pd_{0.99}Fe_{0.01}$ alloy. The MJJ critical current IC can change reversibly due to the magnetic state of the F layer(s), which constitutes a memory cell. A non-destructive readout of such a cell is obtained using SFQ switching. The state of the magnetic layer can be rewritten using a somewhat larger current pulse.

Figure 5A:
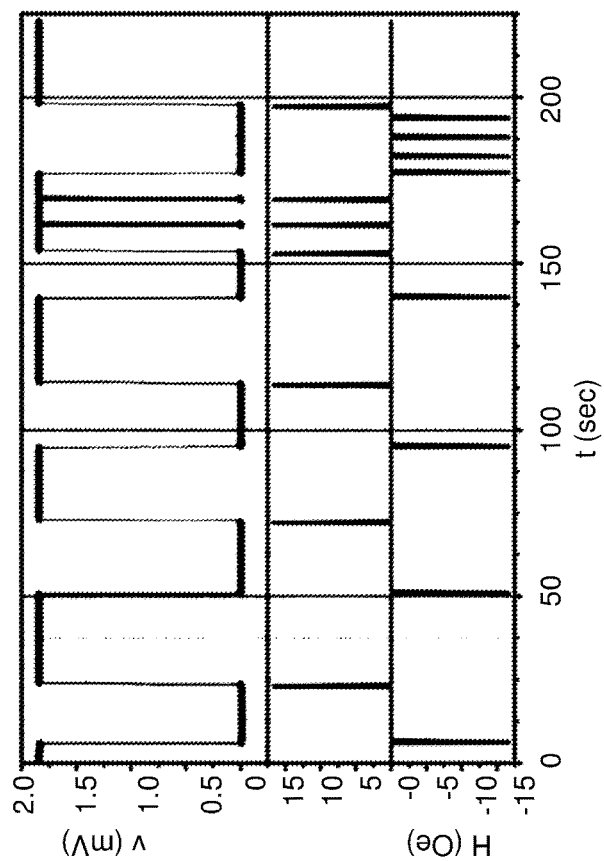
FIGS. 5A and 5B show graphs representing a prototype SIsFS MJJ switched repeatedly back and forth between the zero-voltage and the finite voltage states using an external weak magnetic field.
Figure 5B:
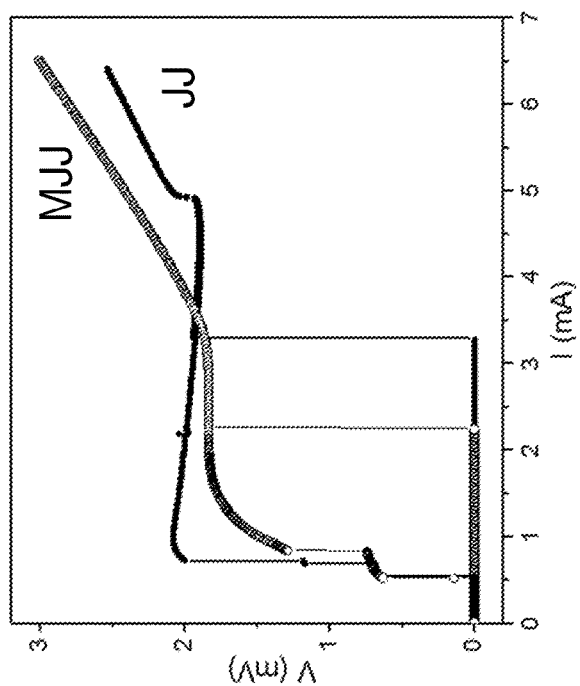

Note that an SIsFS MJJ comprises a series combination of an SIs junction and an sFS junction, but the entire structure behaves as a single junction with a single value of $I_C$. The magnetization of the F layer produces magnetic flux $\Phi$ which is preferably parallel to the plane of the junction, and modulates $I_C$ of the junction. FIGS. 5A and 5B shows an experimental prototype comprising such an SIsFS junction where S and s are Nb, I is $Al_2O_3$, and F is $Pd_{0.99}Fe_{0.01}$, data from T. Larkin et al., "Ferromagnetic Josephson Switching Device with High Characteristic Voltage", Appl. Phys. Lett., vol. 100, 222601 (2012), expressly incorporated herein by reference. Here the V(I) curves are for an MJJ (open circles) and for a similar junction but without the F layer. The switching data on the right show the voltage for an MJJ which exhibits two critical currents $I_{C0} > I_{C1}$, depending on the magnetization of the F layer. The junction is biased at a current I between $I_{C0}$ and $I_{C1}$, so that if the MJJ has the higher value of $I_C$, its voltage is zero ('0' state), while if the MJJ has the lower value of $I_C$, its voltage is nonzero ('1' state). Therefore, a weak magnetic field pulse can switch the MJJ between the '0' state and the '1' state, repeatedly and reproducibly. Specifically, a positive field pulse switches the MJJ from the '0' to the '1' state, while a negative field pulse switches the MJJ from the '1' state to the '0' state. This junction is hysteretic, but it can be converted to a non-hysteretic junction more appropriate to RSFQ circuits, by shunting with a small resistor, as is known in the prior art.

Figure 4:
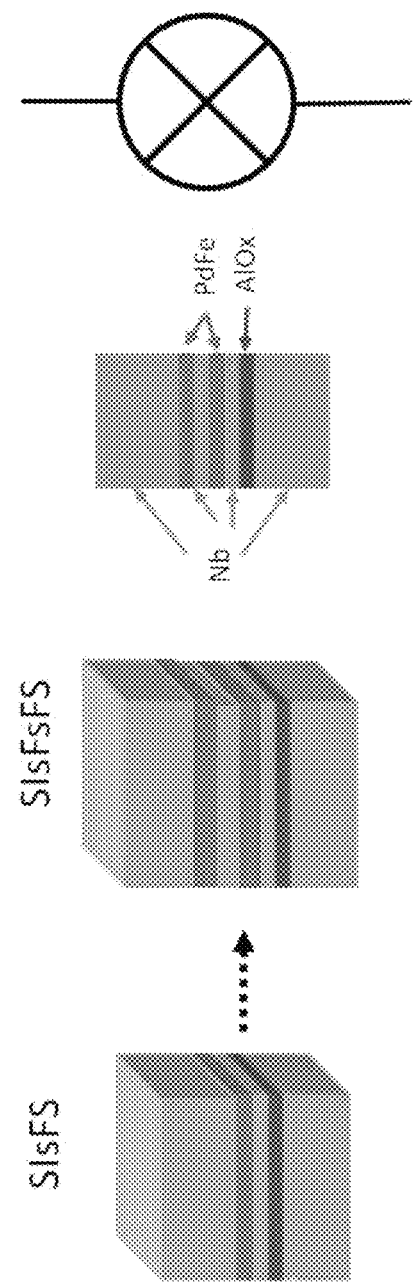
FIG. 4 shows thin-film stacks for several types of MJJ, with the circuit symbol.

A detailed theory of the critical current of similar SIsFS structures was recently presented in Bakurskiy et al., "Theoretical model of superconducting spintronic SIsFS devices", Appl. Phys. Lett., vol. 102, 192603 (2013); and in Vernik et al., "Magnetic Josephson junctions with superconducting interlayer for cryogenic memory", IEEE Trans. Appl. Supercond., vol. 23, 1701208 (2013), expressly incorporated herein by reference. Other recent research (see L. Uspenskaya, et al., "Magnetic patterns and flux pinning in PdFe-Nb hybrid structures", JETP Lett., vol. 97, p. 155 (2013), expressly incorporated herein by reference) has shown that the effective magnetization in the dilute ferromagnetic layer is controlled by the presence of Fe-rich $Pd_3Fe$ nanoclusters, which can be easily reordered by a weak magnetic field. This suggests possible scalability issues of SIsFS memory elements in submicron junctions. Further, the contribution to the net magnetic flux inside the junction becomes smaller with decreasing cross-sectional area of the junction. In order to maintain a flux ~$\Phi_0/2$, the composition and thickness of the F layer may need to be changed in smaller junctions. For example, the Fe content in the dilute PdFe alloy may need to be increased, or alternatively, one could split the F layer into two layers separated by another s layer, creating an SIsFsFS stack. This memory layer progression is shown in FIG. 4. These two F sublayers could be either parallel or antiparallel in their magnetization, corresponding to different values of flux in the junction Another preferred embodiment of the MJJ is shown in FIGS. 24A-24C which incorporates two ferromagnetic layers $F_1$ and $F_2$ in a basic structure $SF_1IF_2S$. In some cases, a thin normal (N) layer (such as Cu) may also be introduced between F layers to decouple them.

Figures 26A, 26B:
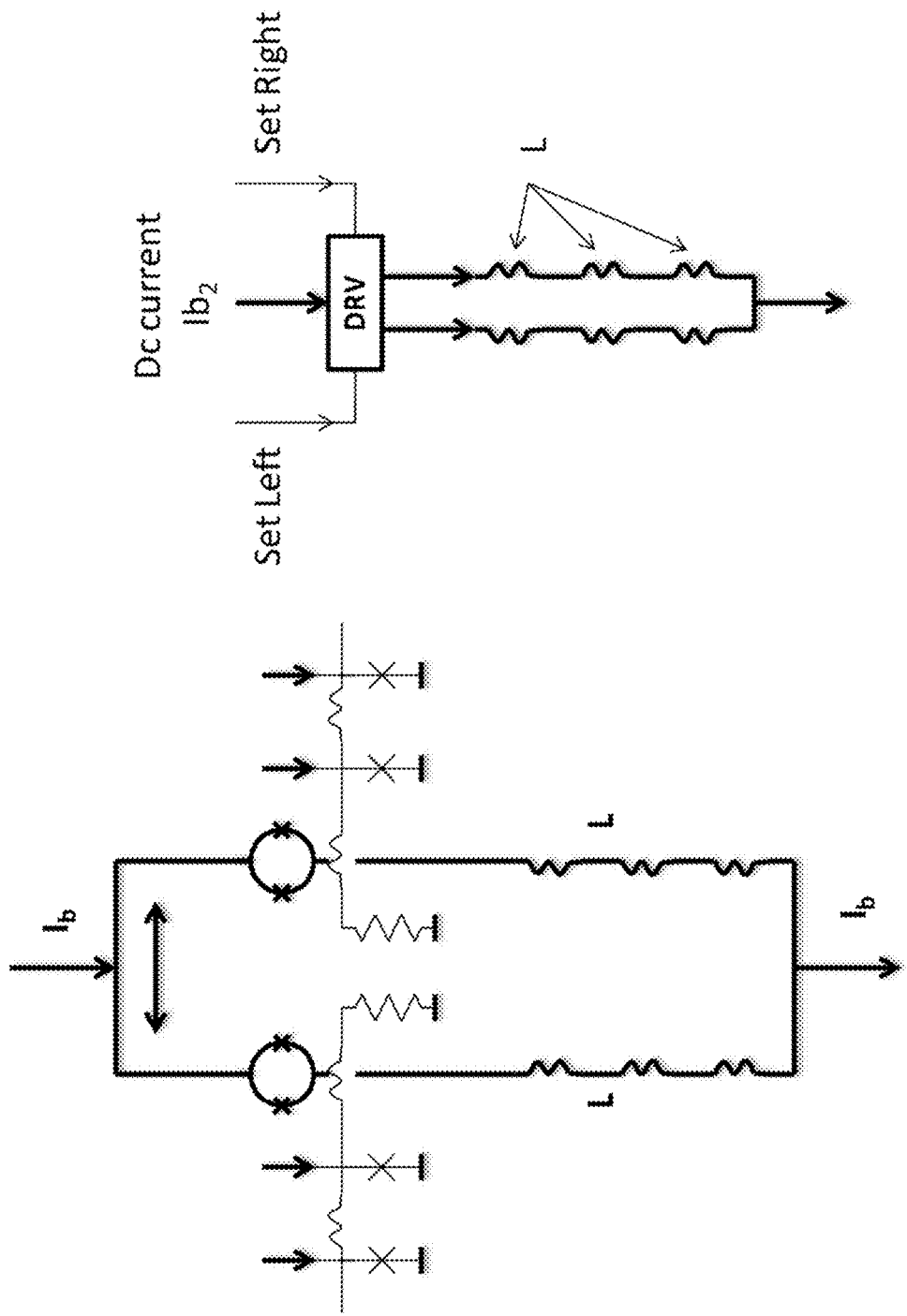
FIGS. 26A and 26B show a schematic for a bit-line driver of a Write circuit for an MRAM array.

FIGS. 26A-26B also show the current-voltage characteristic of a prototype Nb/Ni/AlOx/Ni/Nb MJJ device, 10 µm square, at 4 K. The critical current is strongly modulated with a relatively weak magnetic field, due to the magnetization in the Ni layers. See Prokopenko, et al., "DC and RF measurements of superconducting-ferromagnetic multi-terminal devices", Proc. IEEE 14th Int. Superconductive Electronics Conf. (2013), expressly incorporated herein by reference.

The functioning of this MJJ embodiment is believed to be due to rotation of the magnetization of one F layer relative to the other. For example, the bottom F layer ($F_1$ in FIGS. 24A and 24B) may have a fixed magnetization direction, which may be produced by applying a magnetic field of about 5 mT during layer deposition to establish an easy axis of magnetization parallel to the field. In contrast, the magnetization of the upper F layer ($F_2$) may be able to rotate relative to that of $F_1$. Note that an antiparallel arrangement will correspond to a smaller flux in the junction and hence a higher critical current, as compared with a parallel arrangement.

This rotation of magnetization in one of two magnetic films is similar to the behavior of conventional magnetic spin valves. See, e.g., en.wikipedia.org/wiki/Spin_valve, expressly incorporated herein by reference. Spin valves typically incorporate an extra antiferromagnetic (AF) layer to pin the magnetization of an F layer using the exchange bias effect. An alternative strategy without an AF layer is preferred, whereby $F_1$ is designed to have a higher coercive force than that of the free $F_2$ layer. Hence for a magnetic field exceeding the coercive force of the $F_2$ layer but less than that of $F_1$, the former will switch, leaving the latter unaffected. For example, if a CuNi alloy is used for the F layers, a thin permalloy (Py) layer on the top CuNi layer may lead to a coupled film with reduced coercive field.

A further preferred embodiment of an MJJ comprises a double-tunnel-junction structure that functions as a three-terminal superconducting device, with an injector junction that modulates the critical current of a Josephson junction. The critical current of a conventional Josephson junction may be modulated by an external magnetic field, but that inductive coupling may not be fully scalable to small submicron junctions. The SISFIFS device of FIGS. 6A-6B, also known as a Superconductor-Ferromagnet Transistor or SFT, provides scalable modulation with good input/output isolation. See Nevirkovets, "Hybrid superconductor-ferromagnet transistor-like device", Supercond. Sci. Technol., vol. 24, 024009 (2011), and Prokopenko (2013), expressly incorporated herein by reference. The SFIFS junction represents the injector junction, whereby the introduction of the thin F layer substantially improves the isolation from the SIS acceptor junction. The injector junction may have zero critical current (if the thicknesses of the F layers are large enough), but the acceptor junction may be a standard Josephson junction, which may be non-hysteretic or hysteretic in its V(I) relation. If it is hysteretic, it may be made non-hysteretic using a resistive shunt as is known in the prior art. Very recently, Prokopenko et al (2013) showed 30 dBV input/output isolation and a gain of 1.25.

Figures 6A, 6B:
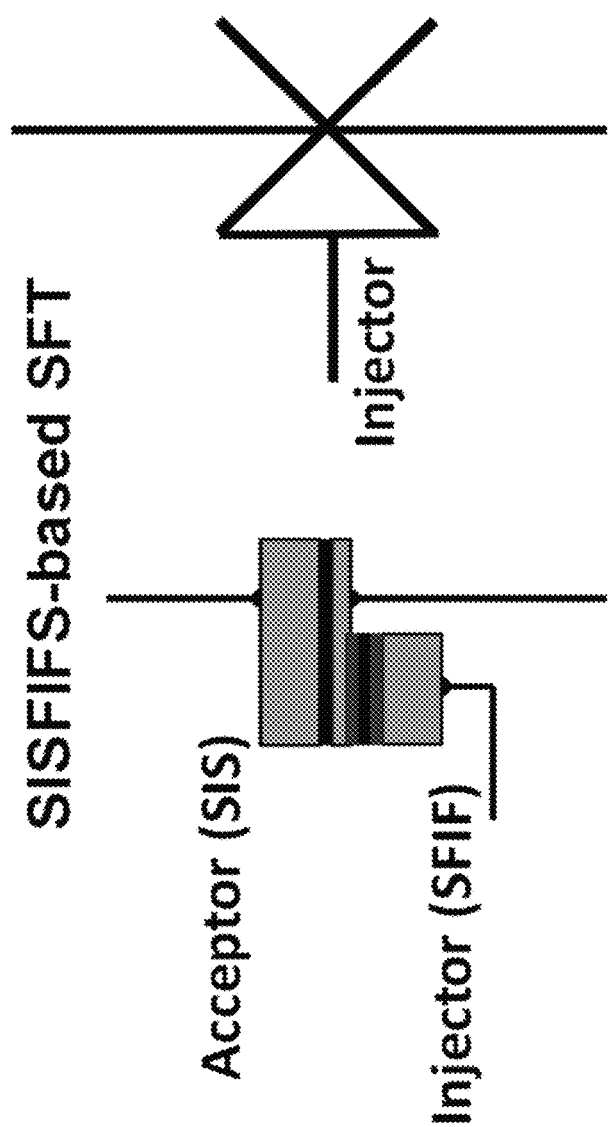
FIGS. 6A-6B show a 3-terminal MJJ structure, the superconductor-ferromagnet transistor (SFT), with a stack SFIF-SIS, where each of the three superconductor layers is a separate terminal, together with its circuit symbol.

FIGS. 6A-6B show the SFQ-MJJ memory cell and a cell array organization in model and schematic form, which may be based on SIsFS junctions. The entire memory cell comprises just a single MJJ. The cells are serially connected to form a bit array column. The key feature of this design is the column layout implemented as a microstrip passive transmission line (PTL) formed by the connected superconducting electrodes of the MJJs over a superconducting ground plane. FIG. 7B shows a perspective view of the layer structure of the SFQ-MJJ cell. This shows the Word Select Line (WL) and Bit Line-Write (BL-W) on top for clarity, although these might be underneath the junction in a real device. The WL is a current line controlled by a JJ-based current-loop line driver; see FIGS. 26A and 26B, described in more detail below. For the Write operation, BL-W and WL current lines intersect with current pulse shapes indicated in FIG. 7C.

Figure 25B:
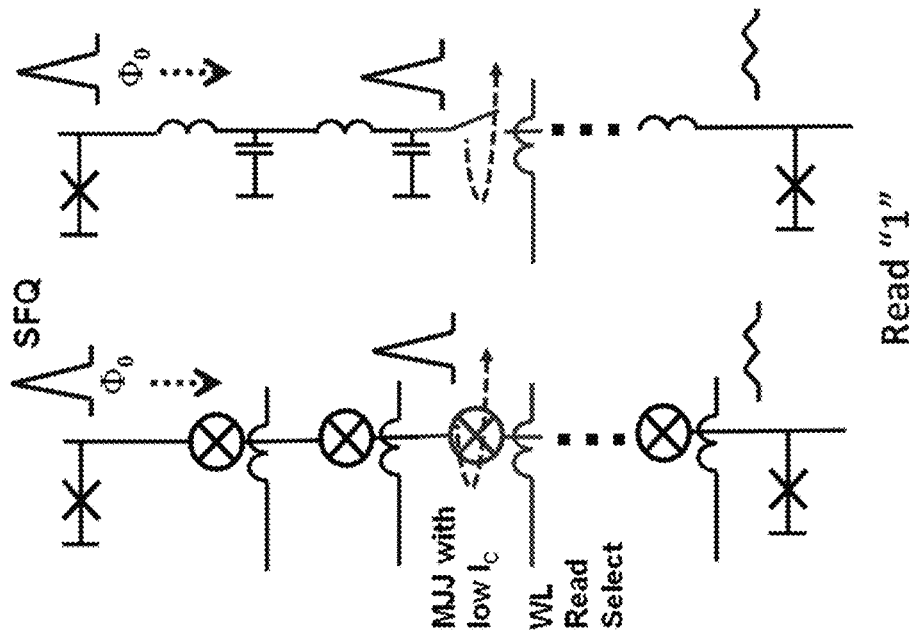
FIGS. 25A and 25B shows the ballistic memory readout architecture for the SFQ-MJJ MRAM of FIG. 7 for a "0" and "1" state, respectively.
Figure 25A:
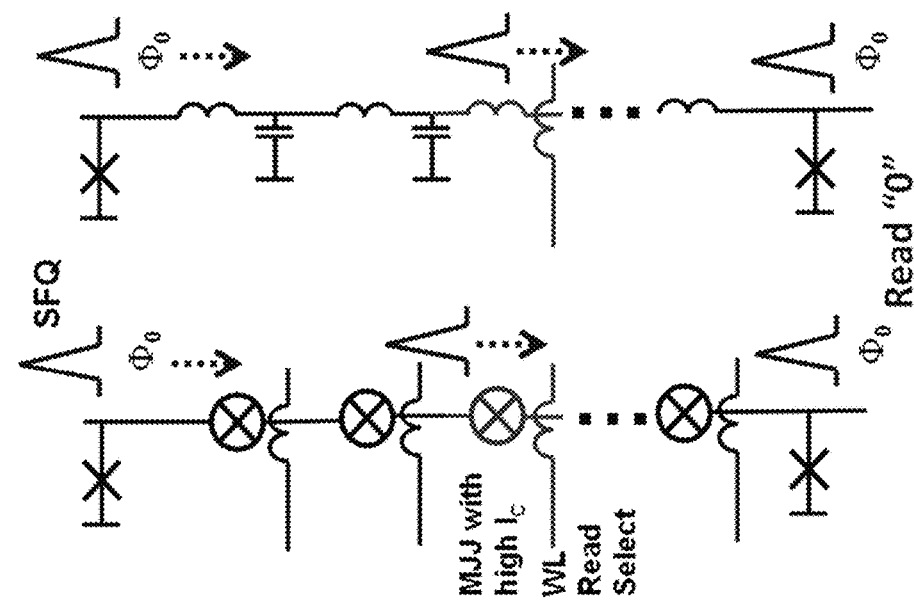

A key innovation of this preferred embodiment of an SFQ-MJJ memory cell is the ballistic SFQ readout (FIGS. 25A and 25B), in which interrogating SFQ pulses propagate along the bit column PTL. In the superconducting state, an MJJ is equivalent to a nonlinear inductor with a Josephson inductance $L_J \sim (\Phi_0/2\pi)(I_C^2 - I_b^2)^{-1/2}$. Each readout column is a PTL comprising the distributed inductance of the junctions and their electrodes, together with the distributed capacitance between microstrips and the ground plane. For the word (row) selection, a WL current is applied to induce a reference magnetic field to the intersecting MJJs. All other rows of MJJs will be in the high-$I_C$ state. This puts the selected MJJs into a state with two clearly distinguishable values of $I_C$, depending on the MJJ magnetization state. If the $I_C$ of the MJJ is high (stored '0'), then the Read SFQ will traverse the MJJ and will continue its propagation down the column PTL to the Sense Circuit on the bottom. If the $I_C$ of the MJJ is low (stored '1'), then the Read SFQ pulse will exceed the $I_C$ of the MJJ, causing the junction to switch, and the SFQ pulse will escape from the PTL. This is equivalent to the PTL temporarily opening, causing the propagating pulse to be destroyed. Simulations show that this process is quite robust, although it will create weak reflections and ripples at the PTL output and input, which can be easily discriminated by the Sense Circuit, which comprises a one-junction SFQ receiver. The Read process is entirely ballistic and is free of half-select problems; energy is dissipated only during reading out a '1'. The critical current of MJJs can be somewhat lower than typical for RSFQ circuits (~100 µA), since the bit-error-rate (BER) of SFQ transmission is quite low. MJJ is projected to be $I_C \sim 10$ µA or even lower, which makes the read energy of a '1' $E = \Phi_0 I_C \sim 10^{-20}$ J.

The cell area of an SFQ-MJJ is very small, less than 1 µm$^2$. Even accounting for a larger pitch to avoid intercell crosstalk in an MRAM array, the resulting density should exceed $10^7$ bits/cm$^2$. These superconducting PTLs should be practically free of loss and dispersion, but if necessary one could include periodic Josephson junction repeaters to regenerate the Read SFQ pulse. For example, one could include two Josephson junctions every 16 MJJs in the column. This would not substantially reduce the MRAM memory density.

The line drivers for the BL-W bit lines are shown schematically in FIGS. 26A and 26B. These are designed using a new energy-efficient current steering technique. The current steering is accomplished using two SQUID self-resetting switches, steering DC current to either of two superconducting bit lines. All bit lines are connected serially and share the same DC bias, with energy dissipated per switching event $\sim LI_b^2/2$. The power dissipation occurs only during a switching event from '1' to '0' or '0' to '1', and power is not dissipated once the switching process is completed. This approach results in substantial power savings compared to prior-art SQUID stack drivers, which dissipated power while the state was '1'.

Figures 27A, 27B:
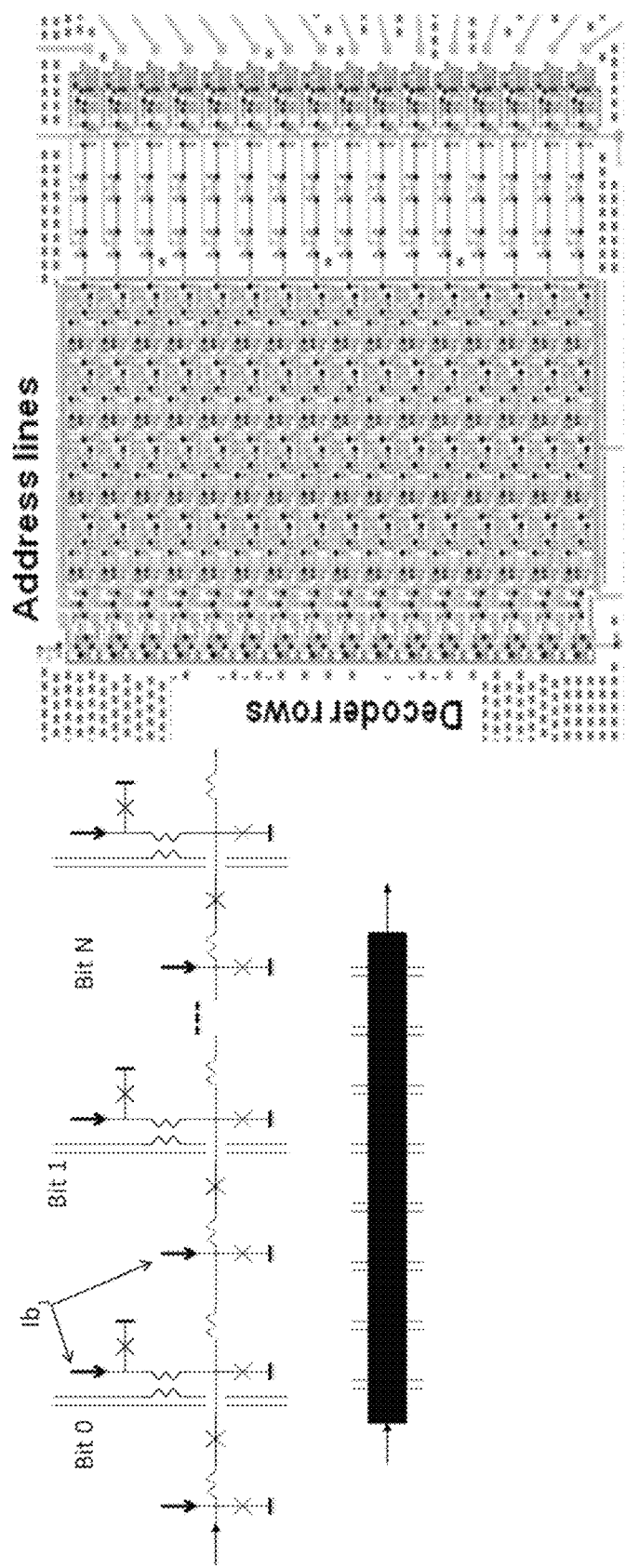
FIGS. 27A and 27B shows schematic of a row of an ERSFQ address decoder for an MRAM array, and a layout of a full decoder.

Another important RSFQ periphery circuit for the MRAM is an address decoder, shown in FIGS. 27A and 27B, which shows the detailed circuit schematic of a single row in FIG. 27A on the left, and the layout of a prototype 4-bit decoder in FIG. 27B on the right. This N-to-$2^N$ decoder was designed using energy-efficient ERSFQ logic, with special attention towards reduction of its circuit complexity and layout area. The required bit decoding function is achieved with only 3 junctions per bit line. The layout of the 4-bit decoder made use of Gray-code addressing, and used only 140 aJ of power. Both power and area are expected to be reduced further in a fully optimized process.

FIGS. 8A-8C shows an alternative MRAM memory architecture that uses SFT-MJJs, where the SFT acts as a cell selector. The SFT-MJJ cell is formed by a single MJJ and SFT cell selector connected in parallel (see FIG. 8A). These cells are serially connected to form an array column. As the SFT has shown excellent I/O isolation, this cell selector may be functionally similar to an FET in conventional room-temperature MRAM cells. FIG. 8B shows the layer structure of an SFT-MJJ memory cell, in which both devices are fabricated in the same in-situ process and arranged vertically. (Further details on the Fabrication are given below.) It is important to note that the SFT-MJJ is not a SQUID, in that the loop inductance is very small, so that the two branches of the Josephson junction are essentially in phase. When the Read current is applied to the BL-Read line, the current splits and distributes in each cell in accordance with the $I_C$ of each branch. Therefore, any reduction in $I_C$ of one branch will redistribute some current to the other branch.

During the Read process, a WL-Read current is applied to the SFT injector in selected Word cells. This action suppresses $I_C$ of the SFT acceptor junction, and increases the BL current portion flowing through the MJJ branch. This current increase is designed so as to trigger the MJJ into a resistive mode if '1' is stored (low $I_C$ of the MJJ), or it will stay in the superconducting state if '0' is stored (high $I_C$ of the MJJ). One can read the corresponding voltages at the top of the BL-Read line using a simple voltage sense JJ circuit. Simulations show that the optimum ratio between the nominal $I_C$ of the MJJ and SFT acceptor is 5:1. This leads to 50% modulation of the $I_C$ of the MJJ, which in turn leads to ±30% margins in the BL-Read current. The voltage across the MJJ will not leak to other word cells (half-selected), nor to any other columns due to the isolating properties of the SFT. The line drivers are identical to those described above for the SFQ-MJJ cell arrays. For the Write operation, intersecting BL-W and WL current lines with current pulse shapes are used, as shown in FIG. 7C.

In this current Readout mode, the energy consumed is somewhat larger than that of the SFQ-MJJ cells using the ballistic SFQ readout, by a factor ~10, but still quite small. The Write energy is essentially the same as for the SFQ-MJJ cells. The cell area for the SFT-MJJ cell will be somewhat larger than that of the SFQ-MJJ cell, if they are fabricated side-by-side as shown in FIG. 7B. However, an alternative fabrication may allow them to be stacked vertically, yielding a very similar bit density ~$10^7$ bits/cm$^2$.

IV. Superconducting Interface Circuits for Spintronic Memory Cells

As an alternative embodiment to MJJ-based memory cells described above, one can use spintronic MRAMs (based on electron spin transfer in magnetic materials) that are specially designed to operate at cryogenic temperatures of 4 K and be compatible with superconducting interface circuits. Preferred embodiments are cryogenic implementations of orthogonal spin transfer (OST) and spin-Hall effect (SHE), and are referred to as COST and CSHE.

Figures 9A, 9B:
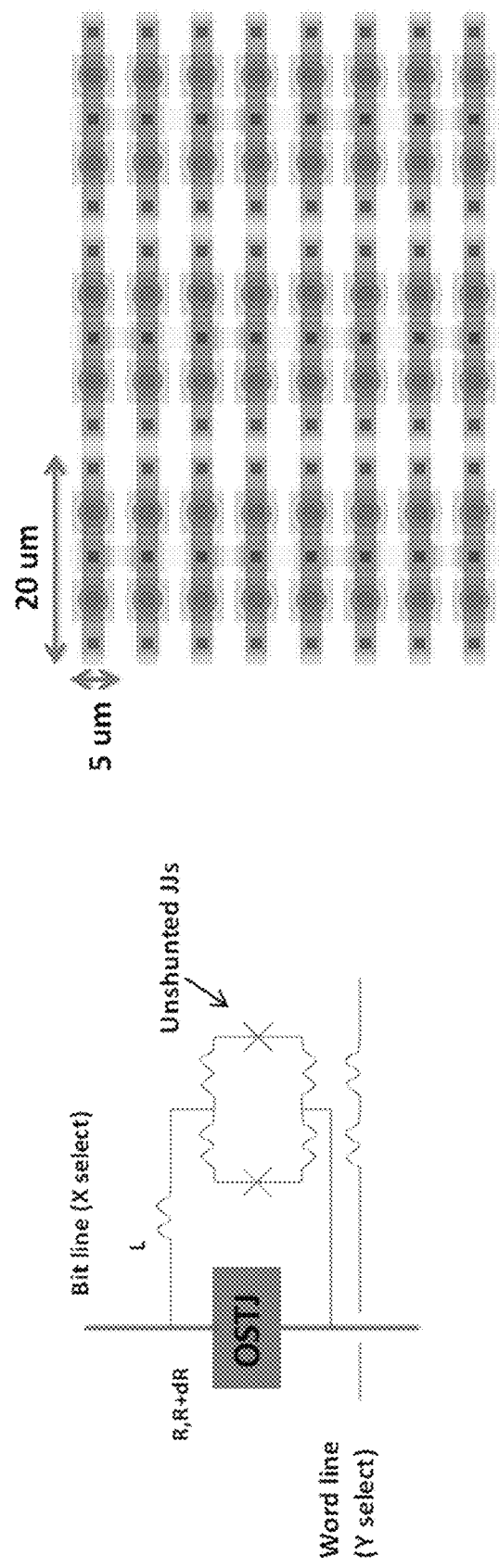
FIGS. 9A-9B shows a further alternative memory cell comprising a COST junction connected in parallel with an unshunted SQUID via an inductance in a configuration known as a Relaxation Oscillator (RO).
Figure 10A:
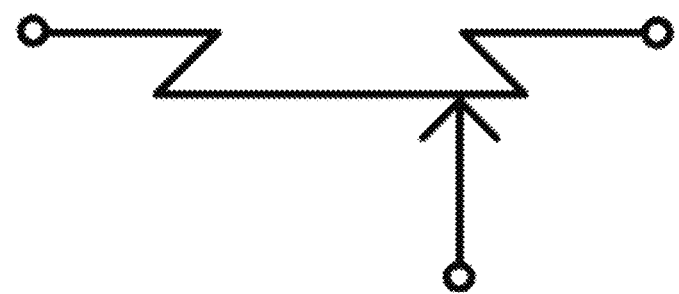
FIGS. 10A and 10B shows a superconductor NanoWire Device (NWD), comprising a narrow superconducting channel (width less than 100 nm) modulated by injection current from a superconducting gate (FIG. 10B), together with its symbol (FIG. 10A).
Figure 10B:
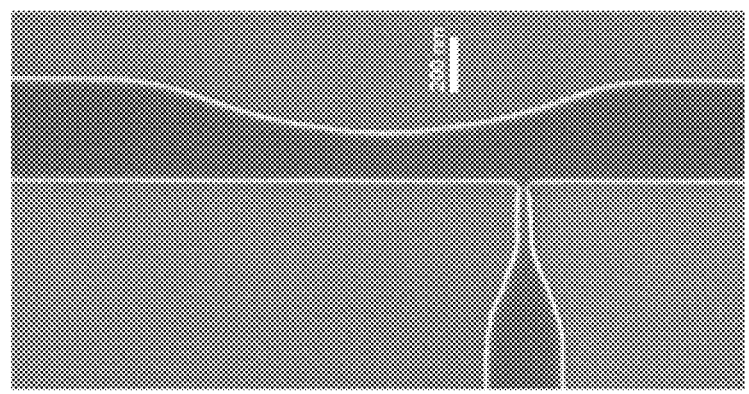
Figure 11B:
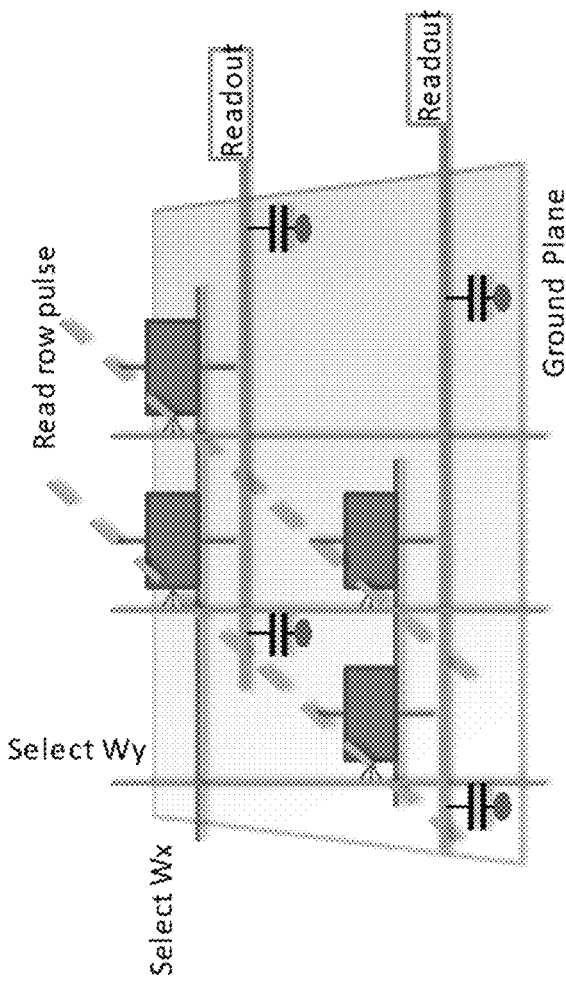
FIGS. 11A and 11B show a hybrid CSHE-NWD cell, where the NWD is the selection element for Write operations, together with a proposed cell array architecture.
Figure 11A:
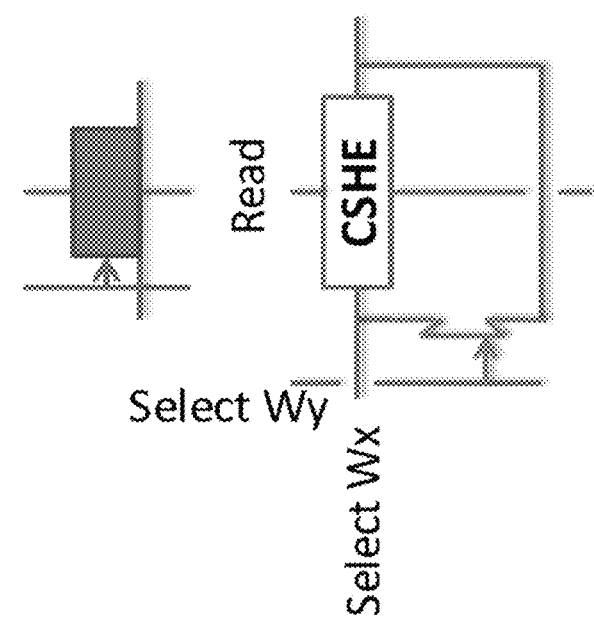

FIGS. 9A-9B show a memory cell that comprises a COST junction (called OSTJ in FIG. 9A) connected in parallel with an unshunted SQUID (with hysteretic Josephson junctions) and an inductance L. When the current from the word line selects the corresponding SQUID, its unshunted JJs switch to the voltage state, forcing the bit line current to flow through the OSTJ. By changing the polarity of the bit line current, we can magnetize (Write '1') or demagnetize (Write '0') the OSTJ. In order to read out, we apply approximately half of the Write current to the bit line and excite the SQUID with a short pulse through the Word line. A SQUID shunted through with an R-L is called a Relaxation Oscillator SQUID (RO-SQUID). See U.S. Pat. No. 5,406,201, expressly incorporated herein by reference. At the value of OSTJ resistance R close to that for critical damping of the SQUID (with McCumber-Stewart parameter $\beta c$~1), the voltage across the SQUID will be either in the shape of an oscillatory relaxation pulse, or a continuous DC offset, depending on the values of R and L. Because of resonance conditions, even a small increase in resistance R stops the SQUID relaxation. This phenomenon can be applied to readout of the memory cell, without any other circuitry. The relatively small resistance of an OSTJ makes this readout quite feasible. Read and Write currents are summarized in Table I below. A drawback to this RO-SQUID readout is the relatively large area associated with the SQUID and inductor, which may be as large as 100 µm$^2$.

TABLE I

Current Parameters for COST cell with RO-SQUID

| | Write '0' | Write '1' | Read |
|---|---|---|---|
| Bit Line | $-I_{write}$ | $+I_{write}$ | $\sim I_{write}/2$ |
| Word Line | $I_{select}$ | $I_{select}$ | $I_{select}$ (short pulse) |

A much more compact superconducting interface circuit for COST and CSHE cells than the RO-SQUID is a three-terminal nanowire device (NWD), illustrated in FIG. 9A. The scale is deep submicron, with a typical channel width ~100 nm or less. An NWD is functionally similar to a traditional FET in semiconductor technology, although it exploits a very different physical phenomenon to achieve switching. It is fabricated in a 2D geometry from a single thin film of superconducting material, typically an ultrathin film of NbN that is highly resistive in its normal state. The three-terminal device is separated into two distinct regions: the gate and the channel. Similar to a non-inverting transistor amplifier, when a logical LOW is fed into the gate input, the channel remains superconducting, and when a logical HIGH is fed into the gate, the channel becomes highly resistive (typically >2 kΩ). Unlike an FET, however, the NWD switching action is controlled by modulating the gate and channel between the superconducting and resistive states. The resistive transition in the channel is induced by locally exceeding the critical current density in the channel, causing current that would otherwise freely drain through the channel to be diverted to the output.

Tests of a prototype device have shown operation for frequencies >100 MHz, with an output impedance of 100Ω, and given the design similarity to superconducting nanowire single-photon detectors (SNSPDs) mentioned above, the device should be capable of approaching at least 1 GHz. Further, previous work on SNSPDs has shown that the device jitter is less than 40 ps, suggesting similar jitter performance for an NWD. This prototype NWD was capable of driving devices with impedances between 10Ω and 10 kΩ, taking a 10 µA signal into the gate and outputting 40-80 µA, depending on the output impedance.

Integration of nanowire superconducting logic will expand the domain of RSFQ, particularly in the area of memories. The device's ability to drive high output impedances will be of particular value to RSFQ integration. NWDs are used here as high-impedance line drivers for connecting RSFQ digital circuits and spintronic memories. Their large current gain may also be used as a way to generate SFQ fanout pulses in RSFQ circuits. The superconducting layer for NWDs may be integrated into a standard RSFQ process, as described below. The same superconducting layer may also function as a high-inductance layer for RSFQ circuits.

Spin-Hall-effect (SHE) memories are being developed for room-temperature operations, see U.S. Pat. No. 7,839,675; 2014/0001524; also WO2014/025838, all expressly incorporated herein by reference. The present application uses versions of these memory cells operating at cryogenic temperatures, known as cryogenic SHE or CSHE.

FIG. 10 shows a symbol and simplified block diagram of memory element based on CSHE, with an NWD-driven select line. The CSHE has low write resistance and exhibits high magnetoresistance. The latter prevents the use of JJs for readout, so an alternative is a "cross-talk" readout scheme described below. The CSHE is a three-terminal device that allows one to decouple Read and Write operations. The NWD may be used as a selection element for Write. The Read operation requires a separate grid of impedance-matched lines for transmitting voltage pulses along a row, while sensing their responses along all columns, thus providing word-parallel memory readout. All of these lines are superconducting passive transmission lines, assuring lossless, dispersionless transmission of pulses, and enabling large memory arrays with low power dissipation.

Figures 12A, 12B:
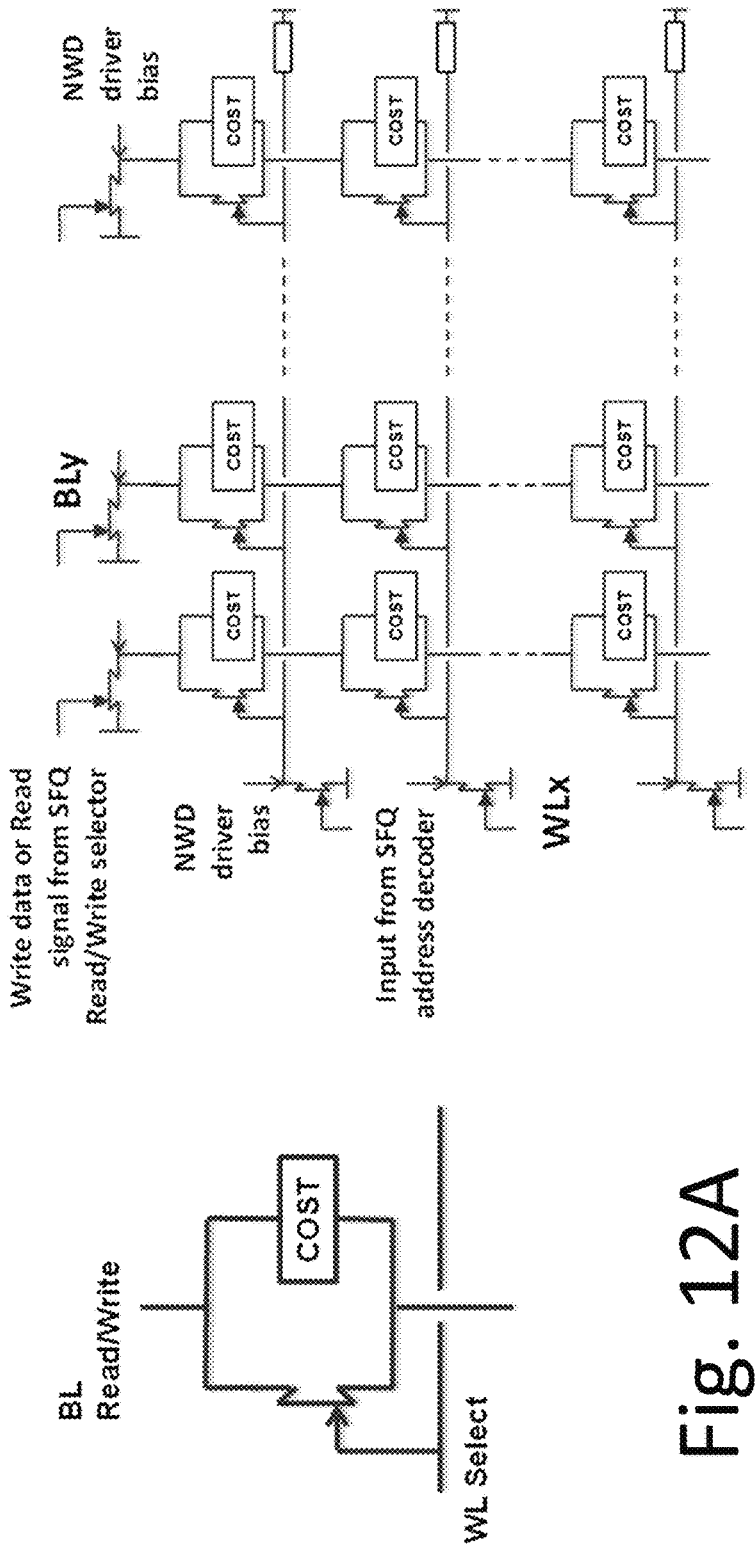
FIGS. 12A and 12B show a COST-NWD memory cell and array.

A similar NWD device may be used as the driver for a COST memory cell, which is a two-terminal device as shown in FIG. 12A. This shows the design of an MRAM memory cell and array based on a combination of COST and NWD devices, together with superconducting read and write lines. The NWD acts as a cell-selecting device functionally similar to an FET in a typical room-temperature spin-torque transfer (STT) MRAM cell. See, for example, U.S. Pat. Nos. 7,170,778; 8,611,117; 8,116,122; 2014/0035617; 2014/0015074, expressly incorporated herein by reference. Once the NWD switches from superconducting to resistive upon activation of the Word Line (WL) Select current, it redirects Read or Write currents to the COST element. Once the WL current is turned off, the NWD selector returns to the superconducting state. The power is dissipated only at the selected cells during Read or Write operations. Since the NWD has a significant power gain, only a very small current is needed to activate the selected NWD. Furthermore, an NWD can be designed with an output impedance that closely matches an optimized COST cell, although it is much higher than the typical impedance for RSFQ. This corresponds to a very high magnetoresistance (MR) close to 100% or above, which in turns leads to a robust memory cell design with high parameter margins. The NWD/COST memory cell circuit area is defined by the COST pillar and the NWD. It is straightforward to integrate both of these side by side within a 2 μm×2 μm area, sufficient to achieve a memory density >$10^7$ bits/cm². It is possible to reduce the cell size even further by fabricating the NWD selector under the COST pillar.

FIG. 12B shows the simplified block diagram of an NWD-COST MRAM cell array. In order to match the higher impedance of the NWD, it is preferable to use line drivers based on similar NWDs biased with AC current. The NWD drivers will redirect the bias current into Word and Bit lines once an SFQ pulse arrives from the RSFQ periphery circuits. The NWD returns to the OFF state once the bias current is reduced to zero. The Read driver can be constructed as a single NWD. For the Write driver, one can use the same driver switched ON for a longer period, or having a larger current amplitude. For a bipolar Write driver, one can use a differential push-pull scheme. The main challenge in the design of NWD-COST MRAM will be to optimize the NWD to respond to an SFQ pulse input. This will be done by designing an SFQ/NWD signal converter.

V. Cryogenic Multi-Chip Module (MCM) for Hybrid Technology Computing System

Figure 13:
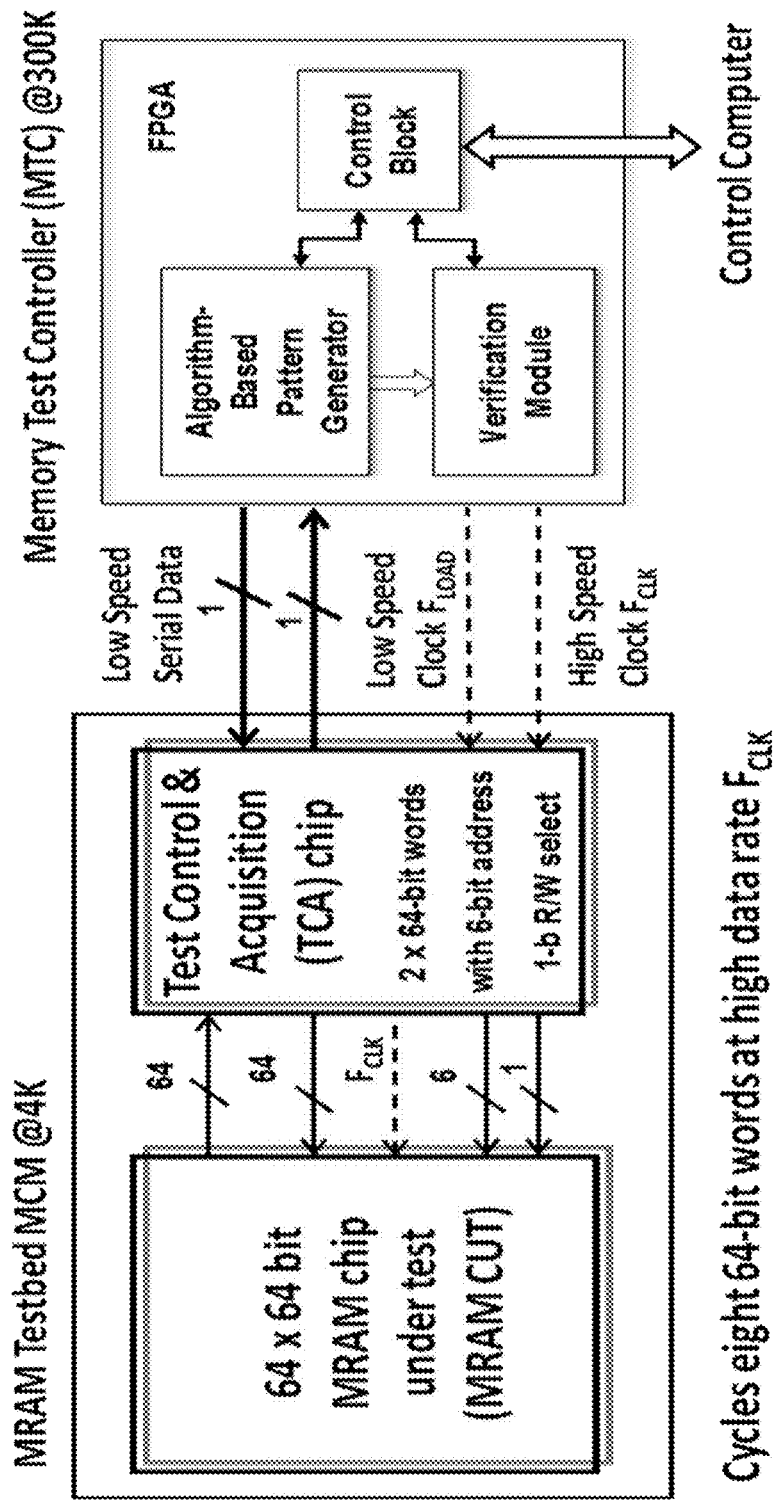
FIG. 13 shows a block diagram for a prototype test system, comprising a cryogenic (4 K) testbed multi-chip module (MCM), and a room-temperature FPGA-based memory test controller (MTC).

In order to communicate between a cryogenic high-speed processor or memory array on the one hand, and a room-temperature system controller on the other, one needs to address an interface problem of sending multiple N-bit words (where N may be 64 bits for an advanced processor), addresses, and control signals between the room-temperature and cryogenic systems. FIG. 13 shows a block diagram of a system to test a prototype superconducting MRAM chip. This requires several key technologies: cryogenic high-speed multi-chip modules (MCMs), cryocoolers and cryogenic system integration, superconducting and semiconducting circuits for multi-rate data and clock operation, interfacing between hybrid electronic technologies, and high-speed data processing on FPGAs. These are many of the same technologies that will be needed to develop a hybrid-technology superconducting supercomputer.

FIG. 13 shows a block diagram of a system for testing high-speed functional operation of a 64×64 bit MRAM chip under test (CUT). The system comprises a cryogenic Testbed MCM (comprises the MRAM chip and a Test Control and Acquisition Chip—TCA) linked to a room-temperature FPGA-based memory test controller (MTC). The communications between the MRAM and the TCA on the MCM comprise 64 parallel bits at high speeds (20 GHz or above), while the communications between the TCA and the MTC are at much lower speeds, and mostly serialized data.

The intention here is to test the performance and yield of multiple MRAM chips, on the same MCM with the same TCA. This requires the use of a reworkable MCM bonding technology for cryogenic chips with multi-GHz signals. See U.S. Pat. No. 8,159,825, expressly incorporated herein by reference. This allows one to successively test multiple MRAM chips by dismounting the tested memory chip without damaging the contact pads of the Testbed MCM. The TCA chip will be mounted using permanent bonding epoxy, as it will not need to be changed.

The FPGA-based MTC is programmed to generate pseudorandom 64-b words and send them to specific addresses in the 64-word MRAM array, and later to retrieve the same words and determine whether there are any bit errors. In more detail, the MTC comprises an algorithm-based pattern generator (to generate the words and the addresses), a verification module (to check for bit errors), and a control block that provides an interface to an external control computer for test summary and evaluation.

Figure 14:
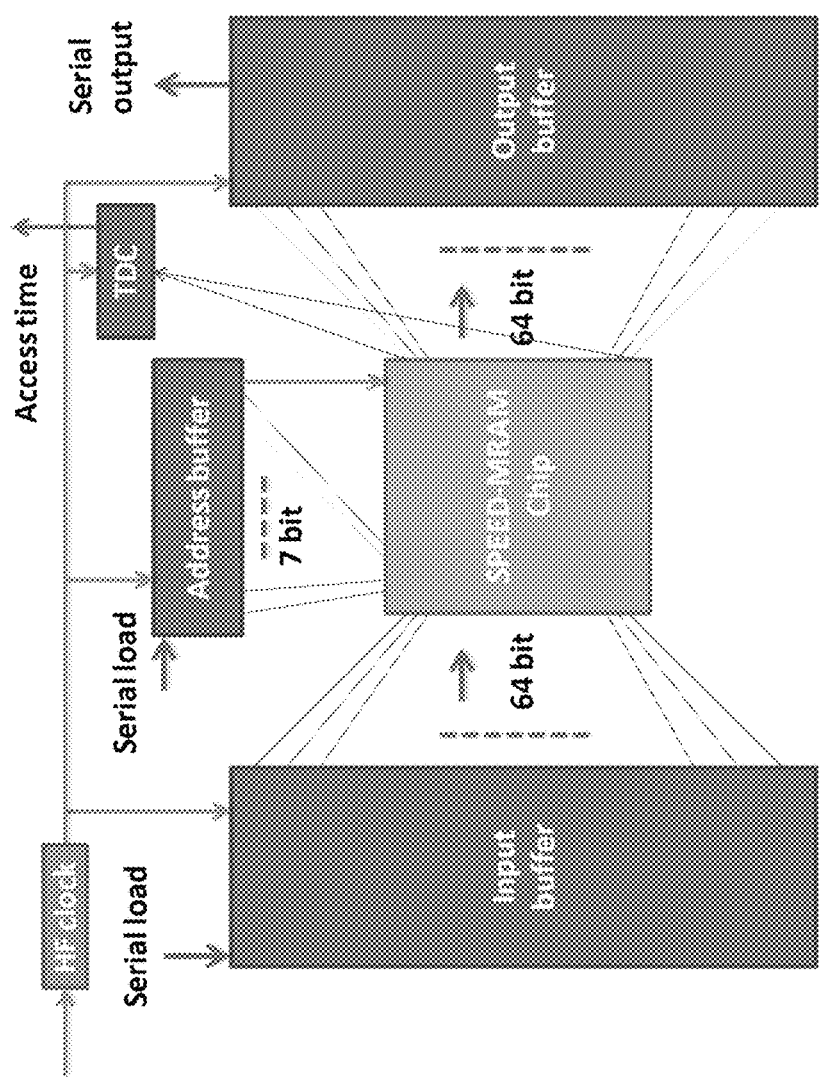
FIG. 14 shows a functional block diagram of the key components of the cryogenic test control and acquisition chip (TCA), which communicates at high speed with the MRAM chip but at lower speed with the room-temperature controller.

The TCA chip (with block diagram shown in FIG. 14) communicates 64-bit data words and addresses serially at low speeds (MHz to 1 GHz) with the MTC module, and communicates the same data in parallel at high speeds (tends of GHz) to/from the MRAM chip. The TCA chip comprises:

High-frequency (HF) clock controller: An SFQ device that produces 8 high-speed SFQ pulses for one test cycle at the trigger from the MTC module.

Input data buffer: A latch-based buffer capable of storing 8 64-bit words. The data are serially loaded via deserializer at low speed. At the signal from the HF clock controller, all 8 words of the test data are sent to the chip under test.

Address buffer: A latch-based buffer capable of storing eight 6-bit addresses and a 1-bit control signal (read/write). As with the input data buffer, it has a serial interface to the MTC module.

Output data buffer: A latch-based buffer capable of storing 8 64-bit words. The 8-word data block read from the memory chip under test are recorded at high speed and then serially uploaded to the MTC module via a serializer at low-speed.

Time-to-digital converter: RSFQ TDC circuit (see U.S. Pat. No. 6,653,952, expressly incorporated herein by reference) for measurement of the MRAM access time (5 ps time resolution).

This test setup will provide flexibility in MRAM testing, allowing test programs to investigate such things as critical test patterns and pattern sensitive faults. In general, there are three classes of errors: bit cell soft errors, hard errors, and transmission errors. Since a cryogenic memory system cannot be tested without the interface link, it is very likely that transmission errors, especially at high data rates, are inseparable from other errors in the system. This system will also permit direct measurement of all memory performance parameters such as cycle time, access time, and access power.

FIGS. 28A and 28B show a configuration of a recent cryogenic test system (for superconducting high-speed digital receiver systems) that may provide a similar cryogenic package to the proposed superconducting MRAM test system. See, e.g., D. Gupta et al., "Modular Multi-function Digital-RF Receiver Systems," IEEE Trans. Appl. Supercond., vol. 21, p. 883 (2011), expressly incorporated herein by reference. The illustrated system was built around a Sumitomo two-stage cryocooler, with a 4 K cold stage and a 50 K intermediate temperature stage. The cryogenic system may use a combination of active and passive magnetic shielding of the MRAM chips and RSFQ circuits. See, e.g., Y. Polyakov, "3D active demagnetization of cold magnetic shields", IEEE Trans. Appl. Supercond., vol. 21, p. 724 (2011), expressly incorporated herein by reference.

Proper high-speed testing of MRAM chips requires data exchange at the level of 64-bit words at full speeds, which may ultimately be as fast as 100 GHz. In general, bit errors of all types increase at high frequencies. RSFQ circuits are characterized by SFQ voltage pulses, with integrated voltage of 2 mV-ps, typically corresponding to a signal ~1 mV high with a pulsewidth of 2 ps. These pulses pass between chips on an MCM, using passive microstrip transmission lines (PTLs), over distances of up to 10 cm or more. This is especially challenging when a parallel word of 64 bits is sent simultaneously. It is virtually impossible to maintain fully synchronous signals over these distances.

Figure 15A:
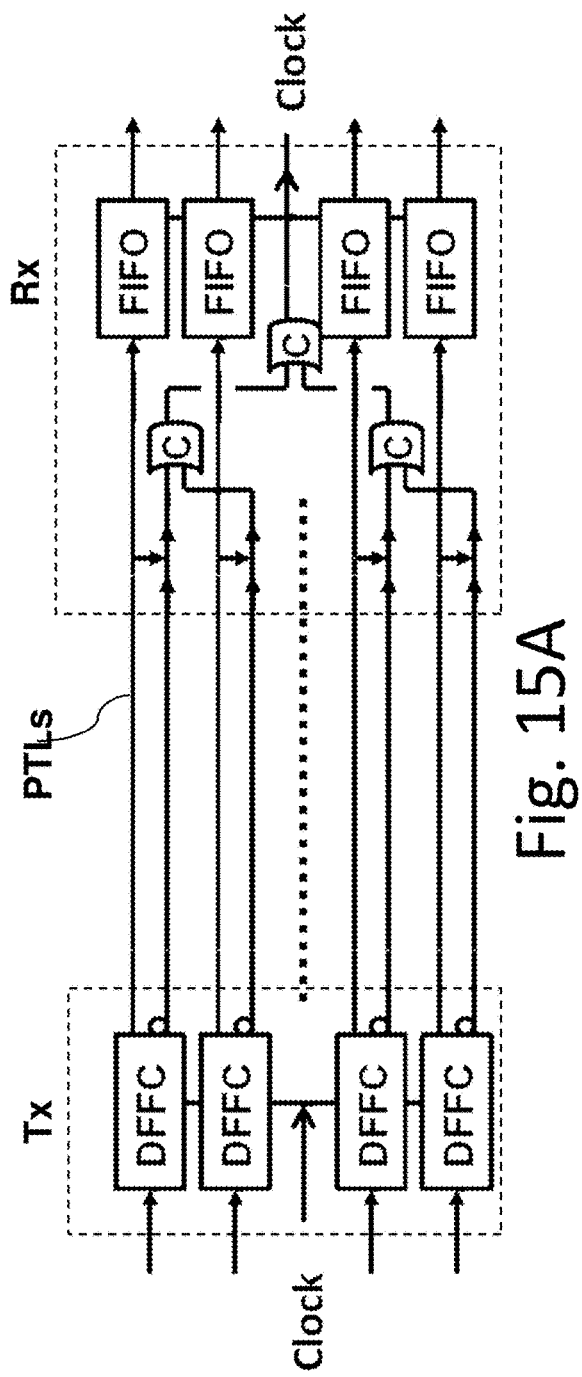
FIG. 15A shows a functional block diagram of bit-parallel chip-to-chip communication on an MCM from a transmitter (Tx) on the left via PTLs to a receiver (Rx) on the right, with clock recovery at the receiver.
Figure 15B:
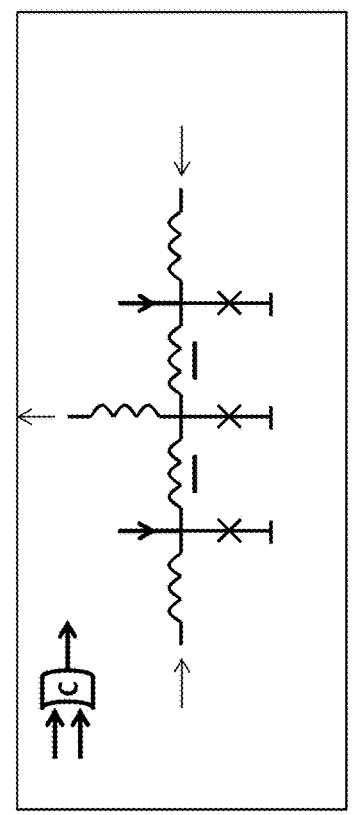
FIG. 15B shows the RSFQ circuit schematic for a Muller-C element.

FIG. 1A5 presents a preferred embodiment of a method for clock recovery when a parallel set of SFQ pulses is sent across PTLs from one chip to another. At the transmit chip on the left, each of the 64 bits has a clocked destructive memory cell, a DFFC, a standard RSFQ cell which is a D-flip-flop with complementary outputs (see pavel.physics.sunysb.edu/RSFQ/Lib/dffc.html). The DFFC has one data input, a clock input, and two outputs, the regular (non-inverting) output (top) and the inverting output (bottom). If the data stored is a '1', the DFFC generates an SFQ pulse from its non-inverting output when triggered. If the data stored is a '0', the DFFC generates an SFQ pulse from its inverting pulse when triggered. This lends itself naturally to dual rail data propagation, where each DFFC always sends an SFQ on one of its two output lines (never both), regardless of the data. At the receive end, the non-inverting output lines are sent to FIFO (first-in, first out) memory buffers. (See, e.g., Herr & Bunyk, "Implementation and application of first-in, first-out buffers", IEEE Trans. Appl. Supercond., vol. 13, p. 563, 2002, expressly incorporated herein by reference.) Further, the 64 bit signals from both '0' and '1' lines are sent to a tree of Muller C-elements (the element with a C, having a schematic shown in in FIG. 15B). The C-element, also known as a confluence buffer, is another standard RSFQ cell (pavel.physics.sunysb.edu/RSFQ/Lib/c.html, expressly incorporated herein by reference) which in this case acts essentially as an asynchronous AND. The final root of the tree generates the new clock which triggers the FIFO buffers, and releases the data to the receiving circuit. This approach ensures that if there is some dispersion in bit arrival, the latching clock is not released until all bits have successfully arrived.

A rapid train of SFQ pulses may maintain its integrity when propagated on lossless superconducting lines at 4K, but these pulses must be substantially amplified to avoid bit errors when propagated on conventional lines at room temperature. This is necessary, for example, in the data sent from the TCA to the MTC. One preferred approach is to provide a cascade of broadband semiconductor amplifiers sending signal on low-loss transmission lines, taking care not to introduce significant noise or heat into the cryogenic system. These transmission lines may comprise high-temperature superconducting electrodes over the colder parts of the data path to room temperature. An alternative preferred approach is to switch to the optical domain at a convenient point, and transmit the signal further via infrared pulses on low-loss optical fibers. Optical signals are well known for the ability to multiplex many signals on the same optical fiber without loss or crosstalk. Optical fibers are also quite compatible with cryogenics, and provide high data throughput with very little heating. Semiconductor laser diodes (such as VCSELs) may be the source of such electro-optical transducers, and fast semiconductor photodiodes may be optoelectronic receivers that convert optical signals back to electrical pulses.

VI. Integrated Circuit Process with Both Superconducting Circuits and MRAM Cells To manufacture hybrid superconducting/MRAM circuits, it is essential to combine the integrated circuit processes for both technologies. This builds on the superconducting IC foundry previously developed at Hypres for Nb-based circuits with a complexity ~10 k Josephson junctions per 1 $cm^2$ chip. Recently, Hypres developed a fabrication process with 6 superconducting layers and planarization using chemical-mechanical polishing (CMP), and adopted a CALDERA process for performing pattern-independent planarization. See U.S. Pat. Nos. 8,301,214; 8,473,818; 8,383,426; 2011/0089405; all expressly incorporated herein by reference. The process involves one CMP step per layer, planarizing the layer as well as the via that connects it to the next layer. The process is integrated with the previous standard process by adding the new layers below the ground plane, and hence enabling extension of the number of layers to 4+n, where n is the number of additional planarized layers. The fact that there is one CMP step makes the process ~20% faster per layer to implement, and integration by extending the number of layers has led us to name the process RIPPLE (Rapid Integration of Planarized Process for Layer Extension). See U.S. Provisional Patent application 61/887,919, "Method for increasing the integration level of superconducting electronic circuits, and a resulting circuit", expressly incorporated herein by reference. The present RIPPLE-2 process with 6 superconducting layers is being extended to a RIPPLE-4 process with 8 superconducting layers, followed by a RIPPLE-6 process with 10 superconducting layers.

In one preferred embodiment, the MJJ/SFT fabrication can be integrated with one of these RIPPLE processes. In order to fabricate MJJ and SFT devices, an existing deposition module with four 4" magnetron sputtering is fitted with two types of ferromagnetic materials: a PdFe alloy (99% Pd/1% Fe) and Permalloy (80.2% Ni/14.7% Fe/4.6% Mo/0.5% Mn). The magnets on the 4" cathodes are upgraded to high-strength magnets in order to enable sputtering of ferromagnetic materials.

Figure 16:
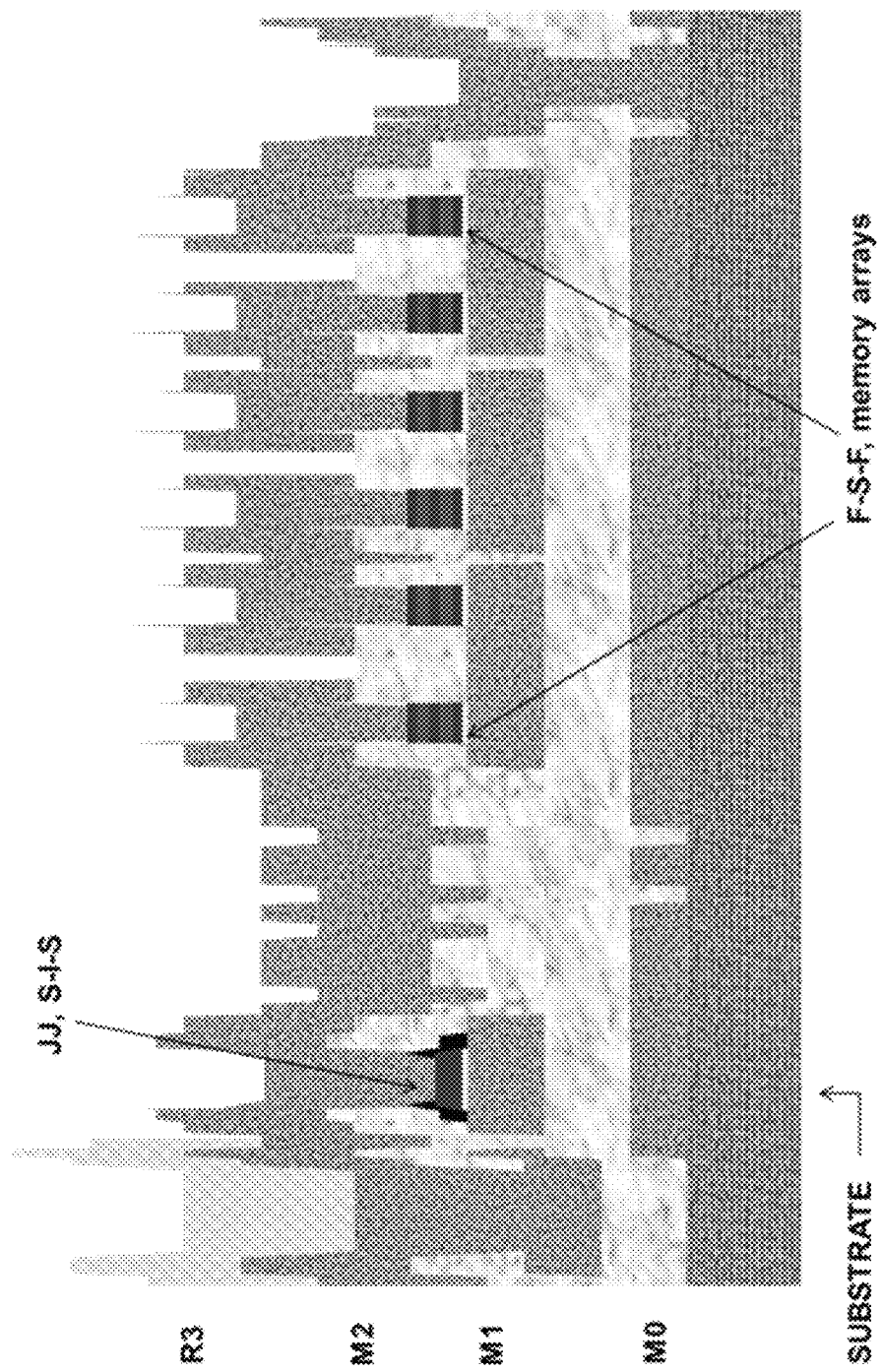
FIG. 16 shows a cross-sectional view of a patterned circuit that comprises both a standard SIS Josephson junction, and also an array of MJJ memory cells.
Figure 17A:
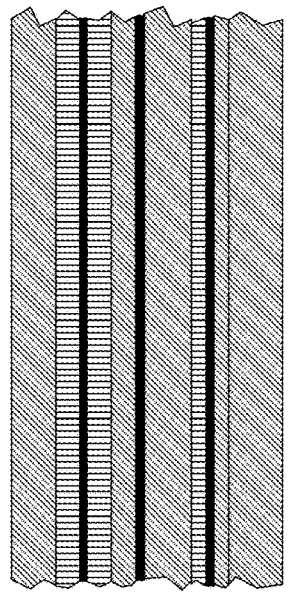
FIGS. 17A-17D show the steps to fabricate a circuit with both an MJJ and an SFT.
Figure 17B:
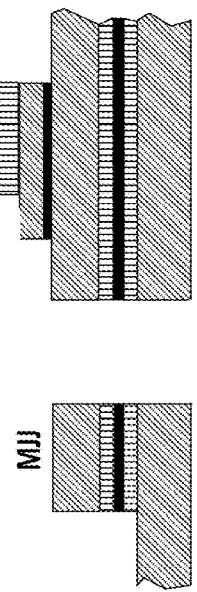
Figure 17C:
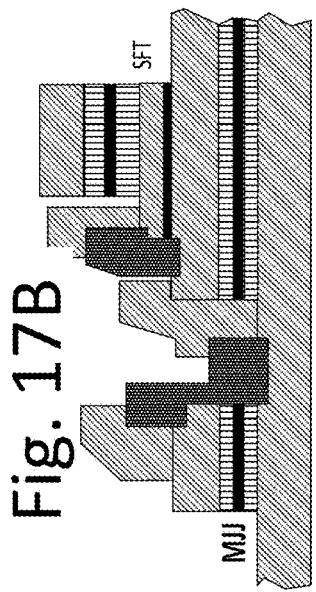
Figure 17D:
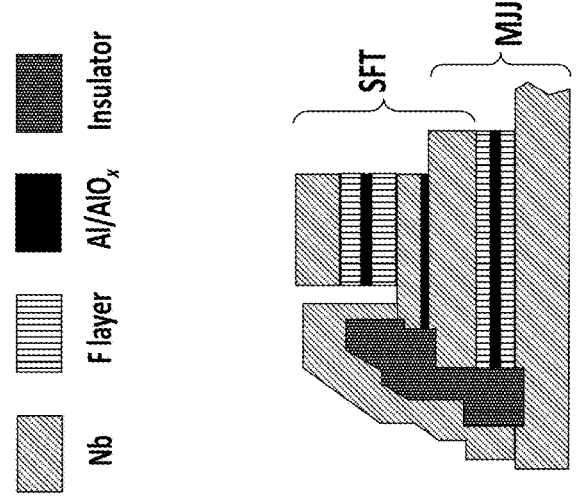

FIG. 16 shows a cross-sectional view of a process that integrates existing planarized superconducting layers with MJJ cells, with additional superconducting wiring layers on top. In order to simplify the fabrication process, it is important to make the MJJ (SFIFS) and SFT (SFIFSIS) multilayer structures in the same deposition run. This can be done by depositing a stack of an MJJ on top of an SFT, i.e., depositing an SFIFSISFIFS multilayer structure in-situ, as shown in FIG. 17A. (The S layers are all Nb, and the I layers may all be AlOx, but the various F layers may be different as discussed earlier.) This stack is processed first to produce an SFT, and afterwards the larger area MJJ, FIG. 17B. Note that the bottom electrode of the SFT is the SFIFS structure. Since the current flows along the top S layer of the SFIFS structure, the F layers and the AlOx tunnel barrier do not play any role here. In the same way one can combine in the same deposition run other device structures, such as SisFS and SIsFsFS. FIGS. 17C and 17D show two ways to integrate an MJJ and an SFT in a memory cell where the MJJ and SIS acceptor junction are connected in parallel. In the first case, FIG. 17C, the MJJ and SFT are situated in-plane next to each other. The wiring layers connect the bottom electrodes of the MJJ and SFT, and the top electrode of the MJJ is connected to the middle layer of the SFT. In the second case, FIG. 17D, the SFT and MJJ are integrated in a stacked geometry. Here the MJJ and SIS acceptor of the SFT naturally share one electrode. The bottom electrode of the MJJ can be connected to the top electrode of the SIS as shown by the slanted via contact in FIG. 17D. This design makes for a very small memory cell, enabling very dense MRAM. Note that FIGS. 17A-17D do not show control lines needed for flipping the magnetization in one of the F layers of the MJJ. These lines would be done using the RIPPLE process, in which the control lines run beneath the memory cell.

In an alternative preferred embodiment, either the COST or the CSHE cells may be integrated with the Josephson junction circuits of the RIPPLE process, and also the NWDs. This is analogous to the proven development path for room-temperature MRAM, in which magnetoresistive devices (such as OST) are integrated on top of prefabricated CMOS wafers.

Figure 18:
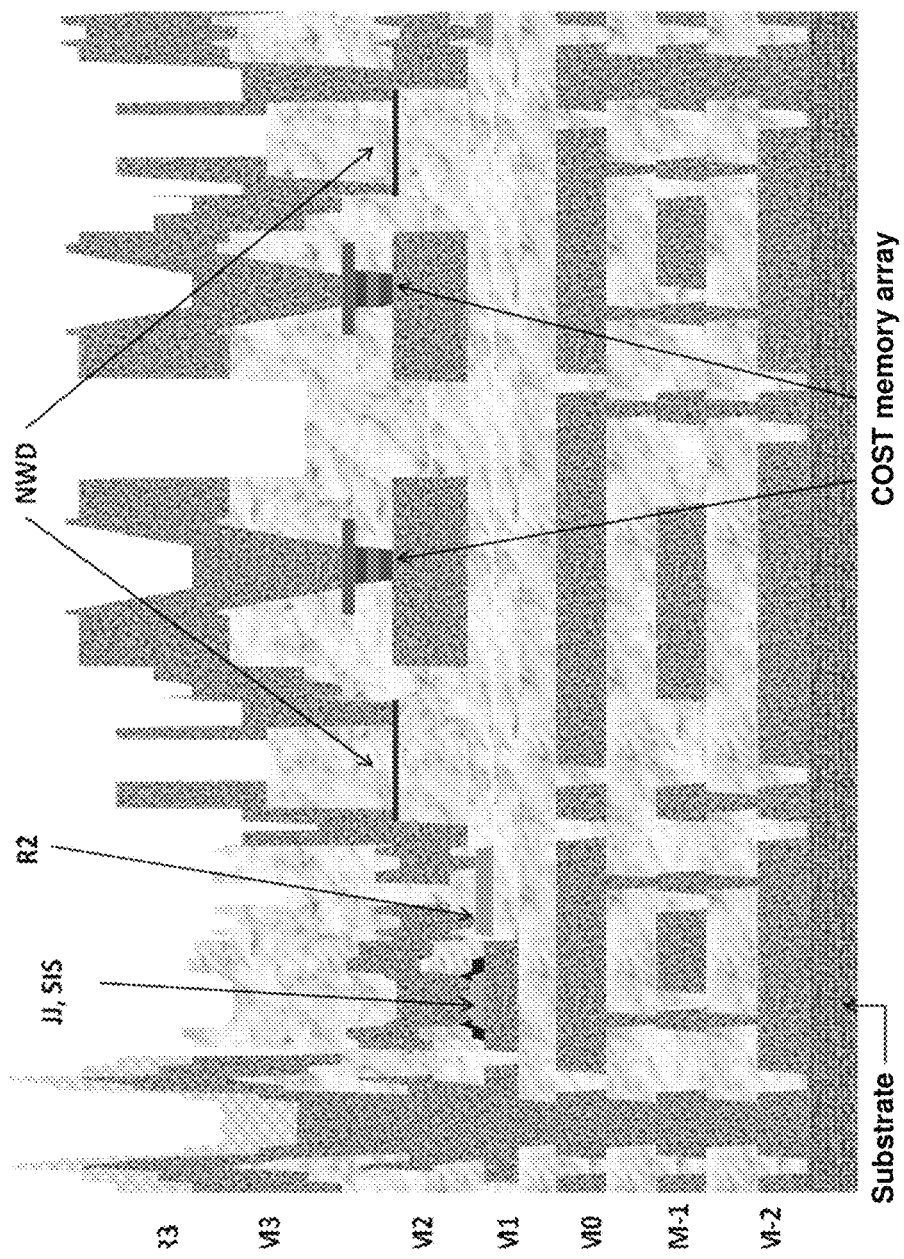
FIG. 18 shows a chip cross section for a circuit in which NWD drivers and COST-MRAM memory cells are fabricated on top of pre-fabricated planarized Josephson junction (RSFQ) circuits.

FIG. 18 shows an example of COST and NWD devices grown on top of planarized superconducting devices, with an additional superconducting wiring layer on top. The NWD layer may comprise an extra thin Nb or NbN layer. A similar process would be used for integrated fabrication of MRAM based on CSHE devices.

The proposed integrated fabrication process is compatible in temperatures, materials, and equipment. Specifically, JJ circuits are sensitive to degradation if the temperature is raised above 200° C. for any part of the subsequent process. Fortunately, the COST fabricated steps do not involve annealing, and no steps require more than 150° C. Furthermore, both JJ and COST devices use transition metals, ensuring compatibility of process materials, process rates and conditions, and equipment. Although contamination of the Nb superconducting process by ferromagnetic materials is possible (and could degrade the superconductivity), this is practically manageable and presents a low risk, as demonstrated in preliminary efforts at process integration.

These detailed examples of preferred embodiments do not imply that this invention is limited only to these examples. Other embodiments of energy-efficient superconducting computers with hybrid memory arrays may also follow from the principles herein disclosed.

What is claimed is:

1. An arithmetic logic unit, comprising a multistage processing pipeline configured to process a received multibit operand through each of a plurality of stages, wherein an arithmetic processing operation within at least one stage is data-dependent on a digital value of the multibit operand, and availability of digital data at a respective stage triggers a commencement of processing within the stage, substantially without time synchronization of the plurality of stages.

2. The arithmetic logic unit according to claim 1, wherein at least one stage is implemented using superconducting device based-logic.

3. The arithmetic logic unit according to claim 1, wherein at least one stage is implemented using rapid single flux quanta-based logic.

4. The arithmetic logic unit according to claim 1, wherein at least one stage is implemented using energy-efficient rapid single flux quanta-based logic.

5. The arithmetic logic unit according to claim 1, further comprising an array of memory cells configured to store data selected from the group consisting of at least one of the multibit operand and a result of the processing operation.

6. The arithmetic logic unit according to claim 1, wherein each respective stage operates asynchronously from each other stage, substantially without a common clock signal between respective stages.

7. The arithmetic logic unit according to claim 6, wherein according to at least one operation performed by the arithmetic logic unit, within a respective stage, a value of a second bit of the multibit operand is dependent on a previously determined value of a first bit of the multibit operand.

8. The arithmetic logic unit according to claim 7, wherein a local clock is provided within a respective stage for coordinating determination of a value of at least the second bit of the multibit operand.

9. The arithmetic logic unit according to claim 1, wherein each stage represents a bit-slice of a multi-bit processor, the multibit operand having an organization representing a plurality of bits of increasing significance, wherein a respective stage determines a value of a respective bit having a significance, and propagates the determined value to an input of a stage having a different significance, wherein processing by the stage having the different significance commences immediately without an interstage synchronizing clock delay.

10. A processor, comprising:
   a superconducting device configured to operate at cryogenic temperatures, organized as a plurality of logic cells in a processing array, each comprising a switchable magnetic material,
   wherein a first cell is configured to logically transform data stored within the first cell and to communicate the logically transformed data to a second cell, and the second cell is configured to commence processing the logically transformed data upon availability from the first cell, substantially without time synchronization with the first cell; and
   an interface circuit.

11. The processor according to claim 10, comprising a multibit arithmetic logic unit having a multistage processing pipeline configured to process a received multibit operand through a plurality of stages, wherein a processing operation within the second cell is data-dependent.

12. The processor according to claim 10, wherein the interface circuit comprises energy-efficient rapid-single-flux-quantum logic.

13. The processor according to claim 10, wherein the multistage processing pipeline comprises an asynchronous wave-pipelined datapath.

14. The processor according to claim 10, further comprising an array of memory cells.

15. The processor according to claim 10, further comprising at least one serial bias circuit, configured to serially bias a plurality of superconducting circuits, wherein the first cell and the second cell are serially biased.

16. A method of processing data, comprising:
providing a multistage processing pipeline configured to process a received multibit operand through each of a plurality of stages, wherein a processing operation within at least one stage is data-dependent on a digital value of the received multibit operand, and availability of digital data at a respective stage triggers a commencement of processing within the stage, substantially without time synchronization of the plurality of stages;
receiving the multibit operand and an instruction;
processing the multibit operand in accordance with the instruction, in multibit operand data-dependent manner, in a first stage;
producing a multibit output of the first stage;
communicating the multibit output of the first stage to a second stage;
processing the multibit output of the first stage, in multibit operand data-dependent manner, in a second stage,
wherein said processing in the second stage occurs asynchronously with the processing in the first stage, substantially without a synchronizing inter-stage clock.

17. The method according to claim 16, wherein the multistage processing pipeline is implemented using superconducting device based-logic.

18. The method according to claim 16, further comprising retrieving the multibit operand from a serially-biased array of memory cells.

19. The method according to claim 16, further comprising generating a local clock signal within a respective stage.

20. The method according to claim 16, wherein each stage represents a bit-slice of a multi-bit processor, the multibit operand having an organization representing a plurality of bits of increasing significance, wherein a respective stage determines a value of a respective bit having a significance, and propagates the determined value to an input of a stage having a different significance, wherein processing by the stage having the different significance commences immediately without an interstage synchronizing clock delay.

* * * * *